US011246820B2

(12) United States Patent
Samain et al.

(10) Patent No.: US 11,246,820 B2
(45) Date of Patent: Feb. 15, 2022

(54) MAKEUP PROCESS

(71) Applicant: L'OREAL, Paris (FR)

(72) Inventors: Henri Samain, Bievres (FR); Franck Giron, Ferrieres en Brie (FR); Guillaume Cassin, Villebon sur Yvette (FR); Véronique Ferrari, Maisons-Alfort (FR)

(73) Assignee: L'OREAL, Paris (FR)

( * ) Notice: Subject to any disclaimer, the term of this patent is extended or adjusted under 35 U.S.C. 154(b) by 434 days.

(21) Appl. No.: 14/368,185

(22) PCT Filed: Dec. 21, 2012

(86) PCT No.: PCT/IB2012/057639
§ 371 (c)(1),
(2) Date: Jun. 23, 2014

(87) PCT Pub. No.: WO2013/093889
PCT Pub. Date: Jun. 27, 2013

(65) Prior Publication Data
US 2014/0345639 A1 Nov. 27, 2014

Related U.S. Application Data

(60) Provisional application No. 61/678,830, filed on Aug. 2, 2012, provisional application No. 61/600,211, filed (Continued)

(30) Foreign Application Priority Data

Dec. 23, 2011 (FR) .................................. 1162377
Dec. 23, 2011 (FR) .................................. 1162384
Dec. 23, 2011 (FR) .................................. 1162430

(51) Int. Cl.
A45D 40/26 (2006.01)
A61K 8/73 (2006.01)
(Continued)

(52) U.S. Cl.
CPC ............ *A61K 8/731* (2013.01); *A45D 33/006* (2013.01); *A45D 34/04* (2013.01); *A45D 37/00* (2013.01);
(Continued)

(58) Field of Classification Search
CPC .... A45D 2200/1009; A45D 2200/1018; A45D 2200/1027; A45D 2200/1036; A45D 2200/1045; A45D 40/261; A45D 40/28
See application file for complete search history.

(56) References Cited

U.S. PATENT DOCUMENTS 5,820,884 A * 10/1998 Klar .......................... A61K 8/26
424/401
5,937,873 A 8/1999 Schlosser et al.
(Continued)

FOREIGN PATENT DOCUMENTS

DE 20212050 U1 11/2002
EP 0779044 A1 6/1997
(Continued)

OTHER PUBLICATIONS

Aug. 2, 2012 Search Report and Written Opinion issued in French Patent Application No. 1162384 (with translation).
(Continued)

*Primary Examiner* — Cris L. Rodriguez
*Assistant Examiner* — Brianne E Kalach
(74) *Attorney, Agent, or Firm* — Oliff PLC

(57) ABSTRACT

The present invention relates to a process for making up the skin, including the step that consists in forming, on a deposit of a foundation composition applied to the skin, a discontinuous deposit of islets of corrective composition and/or a deposit of corrective composition including visible substances that give it an inhomogeneous appearance, said corrective composition having optical properties that locally
(Continued)

modify the appearance of the makeup so as to create a pattern reproducing the appearance of skin relief and/or colour heterogeneities.

36 Claims, 9 Drawing Sheets

Related U.S. Application Data on Feb. 17, 2012, provisional application No. 61/600,005, filed on Feb. 17, 2012.

(51) Int. Cl.

| | | |
|---|---|---|
| *A61Q 1/02* | (2006.01) | |
| *A61K 8/04* | (2006.01) | |
| *A45D 40/00* | (2006.01) | |
| *A45D 33/00* | (2006.01) | |
| *A45D 34/04* | (2006.01) | |
| *A45D 37/00* | (2006.01) | |
| *A61K 8/19* | (2006.01) | |
| *A61K 8/35* | (2006.01) | |
| *A61K 8/36* | (2006.01) | |
| *A61K 8/365* | (2006.01) | |
| *A61K 8/81* | (2006.01) | |
| *A61K 8/89* | (2006.01) | |
| *A61K 8/894* | (2006.01) | |
| *A61Q 1/00* | (2006.01) | |

(52) U.S. Cl.
CPC .............. *A45D 40/00* (2013.01); *A61K 8/046* (2013.01); *A61K 8/19* (2013.01); *A61K 8/35* (2013.01); *A61K 8/361* (2013.01); *A61K 8/365* (2013.01); *A61K 8/8158* (2013.01); *A61K 8/89* (2013.01); *A61K 8/894* (2013.01); *A61Q 1/00* (2013.01); *A61Q 1/02* (2013.01); *A45D 40/261* (2013.01); *A61K 2800/43* (2013.01); *A61K 2800/87* (2013.01); *A61K 2800/884* (2013.01)

(56) References Cited

U.S. PATENT DOCUMENTS

| | | | |
|---|---|---|---|
| 6,235,292 B1 | 5/2001 | Bara et al. | |
| 6,883,995 B1* | 4/2005 | Gueret | A45D 34/04 401/183 |
| 2003/0003064 A1* | 1/2003 | Kalla | A61K 8/11 424/63 |
| 2005/0130536 A1* | 6/2005 | Siebers | A47L 13/16 442/327 |
| 2005/0181067 A1 | 8/2005 | Yokoyama et al. | |
| 2006/0108247 A1 | 5/2006 | Liechty et al. | |
| 2009/0206174 A1 | 8/2009 | Arnaud et al. | |
| 2010/0221294 A1* | 9/2010 | Kurek | A61K 8/027 424/401 |
| 2011/0229247 A1 | 9/2011 | Song | |

FOREIGN PATENT DOCUMENTS

| | | |
|---|---|---|
| EP | 1 030 267 A1 | 8/2000 |
| EP | 1 142 551 A1 | 10/2001 |
| EP | 1 502 574 A1 | 2/2005 |
| EP | 2 361 526 A1 | 8/2011 |
| EP | 2361526 A1 | 8/2011 |
| FR | 2 798 284 A1 | 3/2001 |
| FR | 2 798 286 A1 | 3/2001 |
| FR | 2 816 508 A1 | 5/2002 |
| FR | 2 876 011 A1 | 4/2006 |
| FR | 2 877 819 A1 | 5/2006 |
| FR | 2914625 A1 | 10/2008 |
| FR | 2 949 681 A1 | 3/2011 |
| FR | 2 953 205 A1 | 6/2011 |
| JP | 2001-131024 A | 5/2001 |
| JP | 2001-161436 A | 6/2001 |
| JP | 2004-321814 A | 11/2004 |
| JP | 2009-191070 A | 8/2009 |
| JP | 2011-527591 A | 11/2011 |
| WO | 2003082229 A1 | 10/2003 |
| WO | 2009/075992 A1 | 6/2009 |
| WO | 2011/064719 A1 | 6/2011 |
| WO | 2011/100664 A1 | 8/2011 |
| WO | WO2011100664 * | 8/2011 |

OTHER PUBLICATIONS

Oct. 18, 2012 Search Report and Written Opinion issued in French Patent Application No. 1162430 (with translation).
Oct. 29, 2012 Search Report and Written Opinion issued in French Patent Application No. 1162377 (with translation).
Dec. 12, 2012 Written Opinion of the International Searching Authority issued in Patent Application No. PCT/IB2012/057639.
XP-002685103 The Flawless Starter Kit, http://www.gnpd.com, pp. 456-459.
XP-002685104 Le Blush: mode d'emploi, http://www.madmoizelle.com/blush-98, pp. 1-2.
XP-002685105 My Liquid Blush, http://www.gnpd.com, pp. 1-2.
XP-002685106 Blush, http://www.gnpd.com, pp. 1-5.
XP-002685454 Airbrush Makeup Base System, http://temptu.com/accessories/base-system/basic-system.html, pp. 1-5.
XP-002685455 Enhance Kit Blush & Highlighter, http://www.gnpd.com, pp. 1-7.
XP-002685456 Perfect Complexion Set, http://www.gnpd.com, pp. 1-2.
XP-002685457 A Wrinkle in Highdef Makeup, www.bandpro.com, pp. 1-3.
XP-002718498 Chloé Fall Winter 2011-12 Runway make-up/The Red Dot, http://www.the-reddot.com/2011/03/21/chloe-fall-winter-2011-12-runway-make-up/, pp. 5-12.
XP-002718499 La Berlina: fake freckles, http://laberlina.blogspot.de/2010/02/fake-freckles.html, pp. 1-2.
XP-002718500 ISIS' Wardrobe, http://isiswardrobe.blogspot.de/2009/10/white-skin-and-powdered-hair.html., pp. 1-8.
XP-002685453 Le Fond De Teint, http://web archiveorg/web/20100929051129/http://www.maquillage.com/maquillage/maquillage.php?id=2&page=fond de_teint, pp. 1-6.
XP-002685458 Maquillage Trop de Fond Teint, Lecon de Rattrapage, http://web.archive.org/web/20081123162833/http://www.princesseuh.com/2006/01/trop-de-fond-teint-lecon-de-rattrapage, pp. 1 sheet.
Sep. 22, 2016 Office Action issued in Russian Application No. 2014125003/15(040670).
Feburary 6, 2017 Office Action issued in Japanese Patent Application No. 2014-548323.
Jan. 5, 2018 Office Action issued in Japanese Application No. 2014-548323.
Apr. 25, 2017 Office Action issued in European Patent Application No. 12824729.3.
Jun. 15, 2020 Office Action issued in Japanese Patent Application No. 2019-030562.
Sep. 13, 2021 Office Action issued in Japanese Patent Application No. 2020-139205.

* cited by examiner

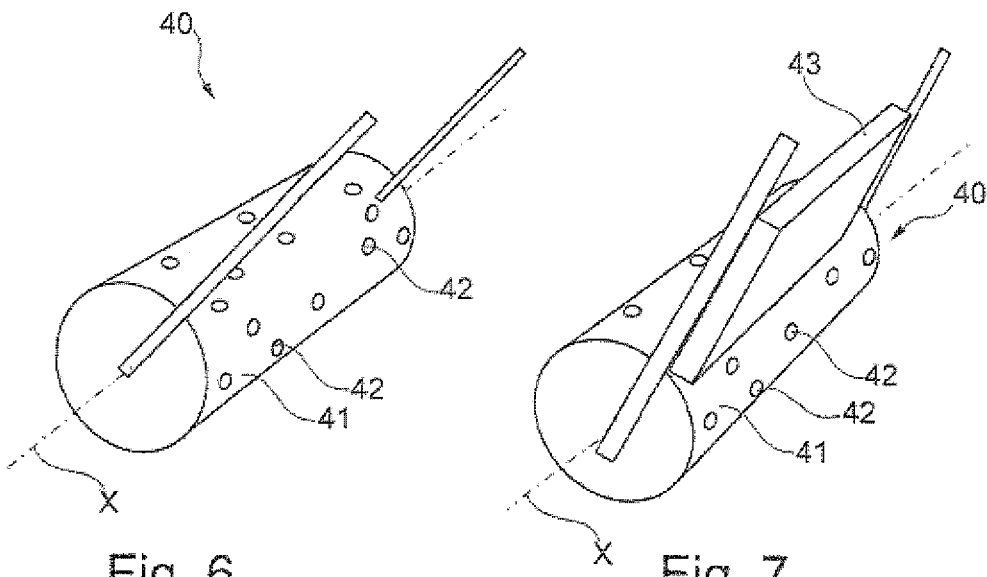
Fig. 6    Fig. 7
Fig. 8
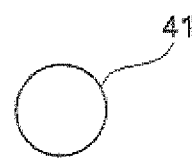    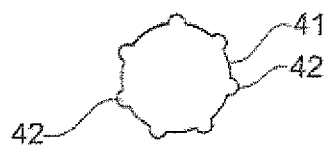
Fig. 9A    Fig. 9B

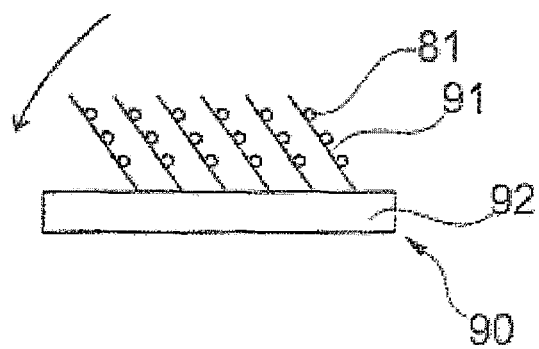
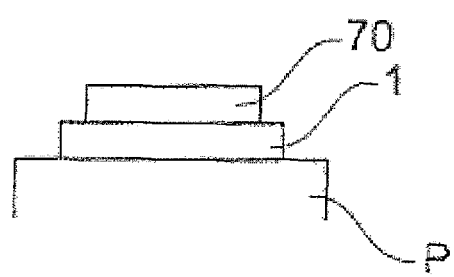
Fig. 14 A
Fig. 15
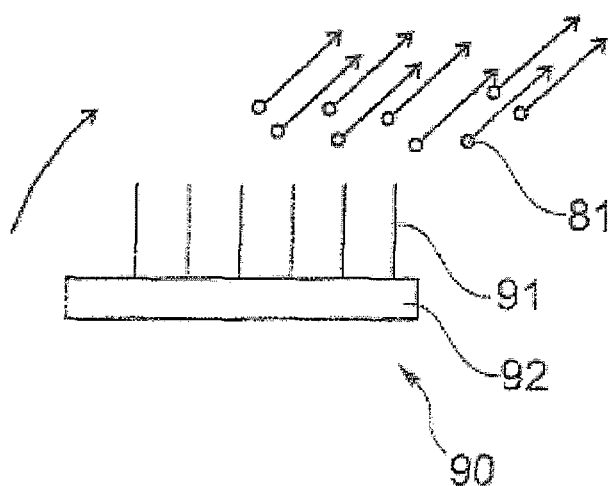
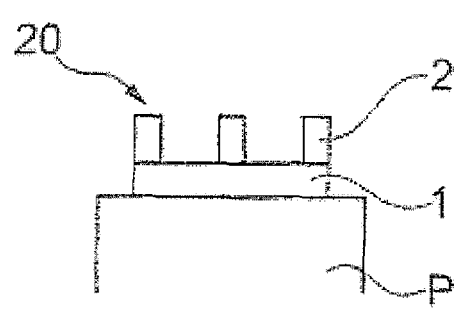
Fig. 14 B
Fig. 16

MAKEUP PROCESS

BACKGROUND

The skin is not a smooth surface of uniform colour, and has reliefs and microreliefs such as pores, fine lines, wrinkles, spots, scars and dry zones, which form a somewhat bumpy surface.

Furthermore, its colour varies on various scales, with blemishes or dyschromias, the differences in colour being sometimes relatively small.

Quite often, this surface, with its irregularities, forms a whole surface that is pleasant to look at, but the irregularities are such that sometimes the surface is judged to be unattractive.

This may stem from a few extra reliefs, or from dyschromias greater than those usually observed. For example, when the pores are slightly more enlarged than in the average case, this tends to render the surface unattractive. Likewise when the dyschromias are broad and/or contrasting.

This may also stem from the fact that the irregularities are poorly distributed. For example, freckles are quite attractive. However, an uneven or asymmetric distribution may make the whole surface rather unattractive.

The irregularities may also be of unequal sizes.

Sometimes, a single irregularity may make the whole of the surface unattractive. For example, a coloured blemish on one cheek may detract from the beauty of the face.

The application of a foundation is the most effective approach for beautifying uneven skin by making it possible to hide blemishes and dyschromias, to reduce the visibility of small reliefs such as pores and wrinkles, and to conceal spots and traces of acne.

However, the presence of a foundation may cause the natural appearance of the skin to be lost, in particular when the product used gives high coverage.

Foundations contain covering particles that provide a colour. Thus, the manufacturers offer these products in various colour variants, giving the user the possibility of finding the product that corresponds to her the best, in particular to chose a shade close to that of her skin.

Another difficulty linked to the use of a foundation is that, by applying the product, all of the irregularities are concealed, namely those that are a nuisance, but also others that it would be nice to keep, which can impart an artificial appearance to the skin.

Formulators have tried to resolve this problem by producing compositions with lower coverage. The transparency of these compositions minimizes the artificial appearance of the skin. However, the user is only partly satisfied with the concealing result.

It is difficult to depart from this logic of compromise between concealing and transparency.

One possibility would be to apply the product only to the imperfection, but this potential solution is very limited in the current state, as it applies only to people who have only small imperfections to cover. Furthermore, it is necessary for these imperfections to be small in number, it being understood that it is tedious to apply the product to a multitude of small zones.

Finally, if the product is only applied to one zone, demarcation problems are created. Obtaining natural or invisible joins requires a lot of mastery. Thus, this solution is not really realistic and therefore most people apply the product to the whole of the face.

The solution proposed by FR 2 933 582 is also known, which is directed towards capturing a grain of skin and reproducing it subsequently on keratin materials. However, the use of the device described in the said document may be relatively expensive.

There is a need to obtain, in a simple manner, a makeup effect that makes it possible to obtain concealing of imperfections while giving the made-up skin a predefined appearance, especially a natural appearance.

The invention aims to meet this need.

SUMMARY

According to a first aspect, the invention relates to a process for making up the skin, preferably facial skin, comprising the step that consists in forming, on a deposit of a foundation composition applied to the skin, a discontinuous deposit of islets of corrective composition and/or a deposit of corrective composition comprising visible substances that give it an inhomogeneous appearance, the said corrective composition having optical properties that locally modify the appearance of the makeup so as to create a pattern reproducing the appearance of skin relief and/or colour heterogeneities.

According to another of its aspects, the present invention relates to a process for making up the skin, comprising the steps consisting in:

a) applying a foundation composition to the skin, and b) locally removing and/or moving the foundation applied in step a) so as to create a pattern reproducing the appearance of skin relief and/or colour heterogeneities.

According to another of its aspects, the invention relates to a cosmetic device with a peripheral surface comprising islets arranged non-uniformly within a surrounding surface, the said islets each having a largest dimension of at least 0.8 mm and having a shape and/or properties for taking up and/or releasing a product present on the skin or for applying thereon a shape and/or properties different from those of the surrounding surface, so as to lead to the creation on the skin of a pattern whose appearance is linked to the arrangement of the islets on the peripheral surface.

The invention advantageously makes it possible to recreate, on the made-up surface, a natural or idealized appearance of the skin, despite the presence of the foundation.

The device advantageously makes it possible to recreate on the skin a natural or idealized skin appearance.

Thus, a makeup, using a foundation that may be relatively covering, advantageously appears less artificial after use of the device on the made-up surface.

The invention makes it possible advantageously to create a relatively set makeup that transfers relatively little.

According to one preferred mode of the invention, the foundation composition dries rapidly, for example in less than 20 min on the skin, via the use of volatile solvents and/or of a high concentration of solids, and/or via the use of film-forming compounds.

By way of example, the foundation composition and/or the corrective composition will advantageously comprise volatile compounds (hydrocarbon-based solvents, hydrocarbon-based oils or silicone oils) representing more than 50%, or even more than 80% by weight, or even more than 90% by weight of the solvent phase. This high proportion of volatile solvents may make it possible to obtain rapid drying of the said compositions on the face and reduced transfer. A longer drying time may nevertheless be sought for the foundation composition, so as to be able to work it by applying the corrective composition or, as detailed below, by taking it up and/or moving it before drying.

The sparingly transferring nature of the foundation composition may, for example, be promoted by the application, after step b), of an intermediary compound that improves the fixing of the makeup, the said compound especially being a fixing lacquer.

The foundation compositions and/or the protective composition may also advantageously comprise at least one film-forming compound (for example: silicone resins, polyacrylates, latices, acrylate dendrimer silicones or reactive silicones) for improving the staying power of the said compositions on the skin and, consequently, for imparting better transfer resistance.

The pattern created reproduces, preferably, the appearance of the user's natural skin texture or a predefined skin texture. The expression "skin texture" should be understood to mean the appearance visible to the naked eye produced by the irregularities in the relief of the skin. The pattern created may reproduce the appearance of the user's natural freckles or of predefined freckles.

In a variant, the pattern created is different from a pattern of a beauty spot. In a variant, the pattern created is not created by a light interference phenomenon.

The device according to the invention makes it possible to create the desired makeup effect relatively simply.

The term "cosmetic device" means that the device is compatible with a use in contact with human keratin materials.

The device may be intended to be brought into contact with a deposit of foundation composition present on the skin in order to create the desired pattern on the said foundation deposit.

The expression "foundation composition" should be understood to mean a covering makeup product.

The covering function may be given by aggregated or non-aggregated particles, typically of the size of a few hundreds of nanometers to a few tens of μm. A covering makeup product may thus generally comprise at least inorganic or organic particulate materials, such as fillers or pulverulent dyestuffs (for example: pigments, nacres, interference particles, and mixtures thereof).

These particles may be included initially in the foundation composition or be obtained extemporaneously by a conversion, for example by crystallization following evaporation of solvent (in the case of a salt), by change in temperature (in the case of a wax or of a semicrystalline polymer), or by chemical conversion (for example reaction between a carbonate and a divalent ion). For example, use may be made of a product that will crystallize like a salt at the solubility limit for which crystallization takes place when the solvent has evaporated or has been absorbed by the skin. It is also possible to use a crystalline polymer that will whiten on evaporation.

More particularly, the foundation composition used in the context of the present invention preferably comprises pigments and, particularly preferably, iron oxides.

The expression "visible substances that give it an inhomogeneous appearance" should be understood as meaning that the visible substances impart by virtue of their optical characteristics, for example colour, gloss or refractive index, an inhomogeneous appearance that is visible to the naked eye without the aid of a magnifying device such as a magnifying glass.

The substances are preferably fibres, and particularly preferably coloured fibres.

The substances may be in the form of an assembly of objects that are isolated from each other, the said isolated objects being visible, or may comprise agglomerates of objects, the said agglomerates being visible.

The substances modify discreetly, for example as a function of their concentration and/or colour, the local appearance of the deposit of corrective composition in order to produce the desired appearance.

The deposit of corrective composition comprising the visible substances, formed on the deposit of foundation composition, may be continuous (i.e. in the form of an integral deposit) or discontinuous.

The corrective composition is preferably coloured and, particularly preferably, comprises a red dye.

Preferably, the process according to the invention comprises the steps consisting in:
 a) applying a foundation composition to the skin, and
 b) applying to the foundation composition the corrective composition so as to form the discontinuous deposit of islets and/or the deposit of corrective composition comprising visible substances that give it an inhomogeneous appearance.

Thus, the corrective composition is preferably applied onto a deposit of foundation composition already present on the skin.

As a variant, the foundation and the corrective composition are applied simultaneously to the skin in order to form the desired makeup.

As a further variant, the corrective composition is first applied to the skin and then, in a second stage, the foundation is applied to the skin so as to totally or partly cover the deposit of corrective composition previously produced. In this case, the corrective composition may be made to diffuse through the foundation coat so as to form the desired makeup. The application of the corrective composition, for example during step b), may be performed with an applicator comprising an application surface that comes into contact with the surface to be made up, especially the foundation deposit, and:
 i) the applicator may comprise a network of zones having corrective composition-releasing properties, the discontinuous deposit obtained being linked to the arrangement of the said zones on the application surface, the said zones present on the application surface of the applicator especially consisting of a network of reliefs and/or holes and/or regions with distinct physicochemical properties, and/or
 ii) the applicator may be brought into contact in a spatially non-uniform manner with the surface to be made up, especially the foundation, so as to obtain the discontinuous deposit of islets of corrective composition.

The corrective composition may also be sprayed onto the surface to be made up, especially onto the foundation deposit, so as to obtain the discontinuous deposit of islets. In this case, the process may comprise, for example before step b), a step of placing a screen bearing holes forming a stencil against the surface to be made up, especially the deposit of foundation composition, and an applicator, especially a sprayer, can spray the corrective composition through the said screen, especially during step b), the discontinuous deposit obtained being linked to the arrangement of the holes in the said screen.

In one implementation example, the invention relates to a process comprising steps consisting in:
 choosing an applicator and/or a screen with holes that makes it possible to obtain a predefined pattern reproducing the appearance of skin relief and/or colour heterogeneities, the choice being made from among a set of applicators and/or screens with holes proposed to the user, and obtaining, on the foundation composition, using the selected applicator and/or screen with holes, the said pattern by using the process defined above.

The set of applicators and/or screens with holes proposed to the user may initially be present in the same makeup assembly, for example in different compartments thereof.

In one implementation example, the invention relates to a process comprising steps consisting in:

selecting a pattern that reproduces the appearance of skin relief and/or colour heterogeneities to be obtained, the choice of the pattern being made from a set of predefined patterns proposed to the user, manufacturing, as a function of the choice made in the preceding step, an applicator and/or a screen with holes that allows the production, on the foundation composition, of the said pattern to be obtained, and obtaining, on the foundation composition, using the selected applicator and/or screen with holes, the pattern to be obtained by using the process defined above.

The set of predefined patterns may, for example, be proposed to the user by means of software. The units may, in this case, be displayed on a display device.

The application surface of the applicator may be manufactured by 3-D printing of a mould thereof, followed by a moulding step.

The application surface of the applicator may be manufactured by laser cutting of a sheet material.

According to another of its aspects, the present invention also relates to an assembly for performing the above process, comprising:

a) the foundation composition,
b) the corrective composition,
c) the applicator for the application of the said corrective composition onto a surface to be made up, especially a deposit of the foundation composition, and
d) optionally, the screen with holes.

The applicator may comprise an application surface comprising a network of zones having corrective composition-release properties which is configured to form, during the application onto the made-up surface, especially onto the foundation composition, a pattern that reproduces the appearance of skin colour and/or relief heterogeneities. As a variant or additionally, the applicator can spray the corrective composition so as to form the discontinuous deposit of islets. The arrangement of the holes in the screen is advantageously linked to a pattern that reproduces the appearance of the skin colour and/or relief heterogeneities to be obtained.

According to another of its aspects, the present invention relates to an assembly for performing the above process, comprising:

a) the foundation composition,
b) the corrective composition, the corrective composition comprising visible substances that give it an inhomogeneous appearance, the said visible substances preferably being coloured fibres.

In one implementation example, the removal and/or movement of the foundation is performed by a device comprising a surface that comes into contact with the deposit of foundation composition, and:

a) the device comprises an assembly of zones for removing and/or moving the foundation, the pattern, and especially the discontinuous network, obtained being linked to the arrangement of the said zones on the surface; these zones present on the surface of the device may especially consist of a set of elements having distinct foundation composition-retaining properties and/or of holes through which the foundation is drawn and/or of reliefs for locally moving the foundation, and/or b) the device is placed in contact in a spatially non-uniform manner with the foundation so as to obtain the pattern, and especially the discontinuous network of islets.

In one implementation example, the foundation is removed by spraying material so as to obtain the pattern, and especially the discontinuous network of islets; the process comprises, before the spraying of material, a step of placing a screen with holes against the deposit of foundation composition and a spraying device sprays material through the said screen. The pattern, and especially the discontinuous network of islets, obtained is linked to the arrangement of the holes in the said screen.

According to another of its aspects, the present invention relates to an assembly especially for performing the process as defined above, comprising:

a) a foundation composition, and
b) a device for locally removing and/or moving foundation deposited on the skin, and
c) optionally, a screen with holes, and
d) optionally, a system for spraying material, the device comprising a surface comprising a network of zones for removing and/or moving foundation so as to form a pattern that reproduces the appearance of skin colour and/or relief heterogeneities, and/or the spraying system for spraying material onto the foundation so as locally to remove the foundation and to form the said pattern, and/or the arrangement of the holes in the said screen being linked to a pattern that reproduces the appearance of the skin colour and/or relief heterogeneities to be obtained.

A subject of the invention is also a makeup kit comprising a device as defined above and a block of a product for loading the device with product to be applied to the skin.

This assembly may comprise a device and a master surface for creating the islets on the peripheral surface, especially a master surface having some zones loaded with product and others without product.

A subject of the invention is also a makeup kit comprising:

a plurality of devices as defined above that differ in the arrangement of the islets within their peripheral surface, and
a block of a product for loading at least one of the said devices with product to be applied to the skin.

Thus, the invention may advantageously enable a user to choose the pattern that he wishes to create on his skin by selecting a particular device in such a kit.

A subject of the invention is also a process for making up the skin, comprising a step of moving and/or taking up a product present on the skin and/or a step of applying a product to the skin using a device as defined above, to create visible zones whose distribution corresponds to that of the islets on the peripheral surface.

The use of the device according to the invention preferably makes it possible to form a discontinuous network of visible zones so as to create the desired pattern.

Visible zones may be created by transferring a product onto the skin, which preferably comprises a red dye.

The visible zones may also be created by taking up product on the skin, the skin having received beforehand the application of a product, preferably a foundation.

The process may comprise the preliminary application to the skin of a foundation. The device may then be used after depositing a coat of foundation, in order to reproduce the appearance of skin grain and/or freckles on the made-up surface.

The treatment using the device is preferably performed without sliding the peripheral surface over the optionally made-up skin, and particularly preferably by rolling the peripheral surface over the optionally made-up skin.

The device is preferably brought into contact with a foundation deposit present on the skin and moved relative to this deposit in order locally to take up the foundation and to obtain the pattern, and especially the desired discontinuous network of visible zones.

In this case, the peripheral surface particularly preferably comprises islets with properties for taking up the foundation present on the skin, which are different from the properties of the surrounding surface.

In one preferred variant, the device is placed in contact with a foundation deposit present on the skin and moved relative to this deposit so as locally to move the said foundation.

In this case, the islets of the device are in relief and protrude relative to the surrounding surface in order for their contact with the foundation to make it possible locally to move this foundation in order to obtain the pattern, and especially the desired discontinuous network of visible zones.

These reliefs have, for example, a height of between 1 and 5 mm and a diameter, measured at the tip, of between 0.3 mm and 5 mm.

In one preferred variant, the device is placed in contact with a foundation deposit present on the skin and moved relative to this deposit in order to apply to the foundation a product so as to form a discontinuous deposit of visible zones and/or so as to apply to the foundation a product comprising visible substances that give it an inhomogeneous appearance, the said product having optical properties that locally modify the appearance of the makeup so as to create a pattern reproducing the appearance of skin relief and/or colour heterogeneities.

Measurement of the Coverage in the Case of Liquid Compositions (at 25° C.)

The term "liquid composition" means a composition whose viscosity can be measured. A liquid composition can flow under the effect of its own weight.

The coverage of the liquid compositions is measured at a finished thickness of 50 μm for the liquid compositions.

The composition is spread onto matt black and matt white contrast cards, for example of Leneta Form WP1 brand for the matt black card and of Leneta 1A brand for the matt white card.

The application may be performed with an automatic spreader.

The measurements are taken on the compositions thus spread out.

Solid Compositions (at 25° C.)

The solid compositions are those whose viscosity cannot be measured.

They may be compositions cast in stick form or pulverulent compositions, in the form of loose or compacted powders.

a) For the pulverulent, loose or compacted solid compositions, the composition is applied using the same contrast cards as above, covered with a slightly rough transparent adhesive tape, for example of the Blenderm® brand from the company 3M and of reference 15025, bonded via the adhesive face onto the contrast cards.

The composition is deposited on the adhesive tape so as to obtain a uniform deposit of 0.5 mg/cm²±0.02 mg/cm².

To perform the deposition, a sponge charged with the composition and mounted on an erosion machine that imposes predefined movements on the sponge may be used. A sponge is, for example, a single-use sponge of Lancôme—Photogenic type, used on the pink side.

b) The compositions in stick form are melted, for example at 90° C., and then spread in liquid form onto matt black and matt white contrast cards, for example of the same references as above, not covered with Blenderm®. The spreading bar is maintained at the same temperature as the composition, so as to avoid a heat shock.

The compositions in stick form are thus deposited, once melted, at a thickness of 50 μm.

Measurements and Calculations

Reflectance spectra are acquired using a Minolta 3700-d spectrocolorimeter (diffuse measuring geometry/8° and observation D65/10°, in excluded specular component mode, small aperture (Creiss)), on the black and white backgrounds, the contrast cards optionally being covered with Blenderm® as indicated above.

The spectra are expressed as colorimetric coordinates in the Commission Internationale de l'Eclairage CIELab76 space according to recommendation 15: 2004.

The contrast ratio, or coverage, is calculated by taking the arithmetic mean of Y on the black background, divided by the mean value of Y on the white background, multiplied by 100.

According to one particular mode, the foundation composition used in the context of the invention has a coverage value of greater than or equal to 30, in particular greater than or equal to 50 and better still preferentially ranging from 60 to 95.

Corrective Composition

As mentioned above, the corrective composition may make it possible to obtain a discontinuous deposit of islets. As a variant, the corrective composition is of inhomogeneous appearance due to the presence of visible substances.

Particulate Corrective Composition

The corrective composition may be a particulate and especially fibrous composition.

The particulate corrective composition may comprise a dyestuff, for example a coloured powder and/or a dye and/or coloured fibres.

As a variant, the particulate corrective composition may comprise an uncoloured material, for example a powder and/or a wax and/or a polymer and/or a salt.

In this case, the particulate corrective composition may produce a relief and/or whiteness and/or gloss effect.

It is possible, for example, to deposit the corrective composition in several distinct points, for example by applying it with a brush. Since the brush is capable of taking up particles on its extremities, the corrective composition can be applied by lightly passing the end of the brush over the surface onto which the foundation composition has been deposited.

In this case, the user can apply the corrective composition onto the deposit of foundation composition in a spatially inhomogeneous manner.

Other types of the applicator may also be used to apply the particulate corrective composition, as detailed below.

Corrective Composition in Fluid Form

As a variant, the corrective composition may be in fluid form during its application to the deposit of foundation composition.

In this case, the corrective composition may comprise a continuous medium, for example a medium in which the visible substances are present.

The corrective composition that is in fluid form during its application may, in one implementation example:

a) comprise visible substances, especially fibres, and/or
b) comprise a volatile solvent, especially a hydrocarbon-based volatile solvent such as ethanol, acetone, isopropanol, propanol, dimethyl ether, methyl ethyl ether, diethyl ether, and/or a hydrocarbon-based volatile oil as chosen from linear or branched $C_8$-$C_{16}$ alkanes (for example: isododecane, isodecane, isohexadecane; a decane, dodecane or tetradecane, or an undecane/tridecane mixture) and/or linear or cyclic silicone volatile oils, especially those with a viscosity of less than or equal to 8 centistokes (cSt) ($8\times10^{-6}$ $m^2/s$) and especially containing from 2 to 10 silicon atoms (for example: decamethylcyclopentasiloxane, dodecamethylcyclohexasiloxane, decamethyltetrasiloxane, dodecamethylpentasiloxane or polydimethylsiloxanes, and mixtures thereof), and/or
c) be in the form of a multi-phase and especially a two-phase composition, one of the phases especially being transparent.

Preferably, the visible substances comprise, and especially consist of, coloured fibres with a mean length of between 0.2 mm and 2.5 mm and/or a mean diameter of between 50 µm and 200 µm.

These fibres may be natural or synthetic, and mineral or organic.

The term "fibre" should be understood as meaning an object of length L and diameter D such that L is very much greater than D, D being the diameter of the circle in which the cross section of the fibre may be inscribed.

The fibres will generally have a length L ranging from 100 µm to 1000 µm, but they may be shorter or longer.

They may be longer especially if the fibres are very fine, for example with a diameter D of less than 5 µm. In this case, the size may range up to 3000 µm.

They may be shorter especially if the fibres are slightly thick, for example with a diameter D of greater than 30 µm. In this case, the lower limit of the size range may be 50 µm.

In particular, the ratio L/D may be between 3.5 and 2500, preferably between 5 and 500 and particularly preferably between 5 and 150.

Use may especially be made of fibres used in the manufacture of textiles, and especially silk fibre, cotton fibre, wool fibre, flax fibre, cellulose fibre extracted in particular from wood, from plants or from algae, rayon fibre, polyamide (Nylon®) fibre, viscose fibre, acetate fibre, especially rayon acetate fibre, poly(p-phenyleneterephthalamide) (or aramid) fibre, especially Kevlar® fibre, acrylic polymer fibre, especially polymethyl methacrylate fibre or poly(2-hydroxyethyl methacrylate) fibre, polyolefin fibre and especially polyethylene or polypropylene fibre, glass fibre, silica fibre, carbon fibre, especially of carbon in graphite form, polytetrafluoroethylene (such as Teflon®) fibre, insoluble collagen fibre, polyester fibre, polyvinyl chloride fibre or polyvinylidene chloride fibre, polyvinyl alcohol fibre, polyacrylonitrile fibre, chitosan fibre, polyurethane fibre, polyethylene phthalate fibre, and fibres formed from mixtures of polymers such as those mentioned previously, for instance polyamide/polyester fibres.

The fibres may be uncoloured or coloured intrinsically or by coating and/or treating the said fibres with an agent that is capable of imparting colour. Such an agent may be chosen especially from cationic, anionic and nonionic dyes, for instance nitro or anthraquinone dyes, or from oxidation precursors used in hair dyeing, or from graftable dyes. Preferably, the colouring agents used are anionic dyes, and especially those bearing sulfonic functions, and also graftable dyes, such as those used in textile treatments.

The diameter of a fibre corresponds to its largest transverse dimension.

In a particularly preferred manner, the visible substances comprise and especially consist of red-coloured or violet-coloured fibres.

Use may be made, for example, of the fibres used in documents JP2007210894, JP2007077098, JP2006052203 and JP2006052202.

In one implementation example, the corrective composition comprises coloured grains dispersed in a medium, which may be sparingly coloured or uncoloured.

Such a composition may be applied to the skin by transfer using applicators as described below.

The coloured grains may have a size of between 0.3 mm and 2 mm and especially between 0.5 mm and 2 mm.

The grains may be made of a material chosen from glass, zirconium oxide, tungsten carbide, plastics such as polyurethanes, polyamides, polytetrafluoroethylene or polypropylene, metals such as steel, copper, brass or chromium, marble, onyx, jade, natural mother-of-pearl and precious stones (diamond, emerald, ruby or sapphire, amethyst or aquamarine). Glass beads are advantageously used: use may be made, for example, of the products sold under the reference Silibeads® by the company Sigmund Lindner, these beads having the advantage of giving the makeup a glossy effect. The coloured grains may be deformable or undeformable, solid or hollow, and coated or uncoated.

These particles are initially coloured, or are post-treated so as to give them a colour or to modify their colour, for example by impregnation in a colouring composition.

The medium may be a carbopol gel, a guar gum gel or an emulsion.

When the corrective composition is in liquid form during its application, it may be applied by transfer onto the foundation composition by means of an applicator. As a variant, the correct composition may be sprayed onto the foundation deposit as will be detailed hereinbelow.

Application in the Form of Droplets

When the corrective composition is in liquid form, it may be applied to the foundation composition in the form of droplets.

In this case, the corrective composition may comprise a mass content of solids ranging from 0.01% to 100%. In this case, the corrective composition may be sprayed and may optionally comprise a solvent, typically ethanol or a silicon-based or carbon-based solvent.

The use of such solvents may advantageously enable the production of drops that dry quickly.

The corrective composition may have surface and drying properties that can minimize its spreading on the surface.

Surface Tension Phenomenon

It is possible, in this case, to apply the corrective composition in the form of a continuous deposit, and the discontinuous deposit of islets may be obtained via a surface tension phenomenon.

In this case, a corrective composition whose surface tension is higher than the surface tension of the surface may be used. Preferentially, the difference is at least 3 points and preferably 10 points (the surface tension is expressed in mN/m). For example, since the surface of the foundation composition is slightly hydrophobic, due to the presence of fatty substances such as isododecane (surface tension=25 mN/m approximately), the corrective composition has a surface tension of at least 28 and preferentially greater than 35 mN/m. Preferentially, the corrective composition has a surface tension of greater than 50 and is, for example, a water-based or predominantly water-based composition.

In this case, the mass content of solids may range from 0.01% to 90%.

When the discontinuous deposit is formed by a surface tension phenomenon and when the corrective composition comprises a dyestuff, the mass content of solids in the corrective composition may range from 0.01% to 100%.

When the discontinuous deposit is formed by a surface tension phenomenon and when the corrective composition does not comprise a dyestuff, the mass content of solids in the corrective composition may range from 1% to 100%. Such a corrective composition may be applied by hand or by spraying.

Multi-Phase Corrective Composition

As mentioned hereinabove, the corrective composition may be in the form of a multi-phase and especially a two-phase composition.

In this case, one of the phases may comprise a dyestuff or an uncoloured material (powder or wax or polymer or salts or other materials). For example, the corrective composition may comprise two immiscible liquids, one of which contains a dye or a polymer.

Preferentially, one of the phases is transparent.

In this case, the mass content of solids may range from 0.01% to 90%.

When the corrective composition is multi-phase and comprises a dyestuff, the mass content of solids may range from 0.01% to 90%.

When the corrective composition is multi-phase and does not comprise a dyestuff, the mass content of solids may range from 1% to 90%.

A solids concentration ranging from 0.01% to 90% is used, depending on whether a coloured or uncoloured material is used.

The multi-phase corrective composition may be applied by hand or by spraying.

Independently of the galenical form of the corrective composition, the fibres present in the corrective composition may advantageously have all or some of the following characteristics:
  a) the fibres have a length of between 1 μm and 10 mm and preferably between 0.5 and 5 mm, and/or
  b) the fibres have a cross section inscribed in a circle with a diameter of between 10 μm and 1000 μm, and/or
  c) the fibres produce at least one optical effect, especially in terms of colour and/or gloss and/or relief.

In general, the corrective composition may be applied by hand, by spraying, with an aerograph or with an applicator intended to deposit the corrective composition by transfer onto the surface to be made up, especially the foundation composition.

Discontinuous Deposit of Islets

The discontinuous deposit of islets may comprise islets that are touching and islets that are separate. As a variant, the discontinuous deposit of islets may consist of a set of separate islets.

The discontinuous deposit of islets preferably has all or some of the following characteristics:
  a) the islets have a mean size of between 0.05 mm and 3 mm, preferably between 0.1 mm and 1.5 mm and particularly preferably between 0.3 mm and 0.9 mm, and/or
  b) the mean distance separating two adjacent islets is between 0.25 mm and 20 mm, preferably between 0.5 mm and 5 mm and particularly preferably between 1.5 mm and 2.5 mm, and/or
  c) the discontinuous deposit comprises at least 5, preferably at least 10, preferably at least 30 and particularly preferably at least 100 islets.

The size of an islet corresponds to its largest dimension.

The mean size of the islets corresponds to the arithmetic mean of the sizes of the said islets. The distance between two islets corresponds to the distance separating the barycentres of the said islets.

The mean distance between two adjacent islets corresponds to the arithmetic mean on the number of pairs of adjacent islets of the distances separating two adjacent islets.

Unless otherwise mentioned, the sizes of islets and distances separating two islets are measured at the time of application of the corrective composition.

The density of islets in the discontinuous deposit is preferably greater than 5 islets per $cm^2$ of surface area of skin covered with the foundation, and less than 1000 per $cm^2$.

A discontinuous deposit of islets having:
  islets with a mean size of between 0.4 and 4 mm,
  a mean distance separating two adjacent islets of between 1 and 5 mm,
  a number of islets greater than 1 per $cm^2$,
is preferably obtained so as to form a pattern that reproduces the appearance of freckles.

The islets are preferably non-reflective. The discontinuous deposit of islets preferably does not consist of a deposit of glitter flakes on the foundation.

The islets are preferably applied according to a predefined pattern as detailed hereinbelow.

The appearance linked, for example, to freckles may advantageously be reproduced by creating a discontinuous deposit of islets having at least two regions within which the islets differ in at least one of their appearance characteristics.

Thus, the discontinuous deposit may comprise a first and a second region, the islets present in the first and second regions differing in at least their colour and/or mean size and/or density and/or shape and/or gloss.

Preferably, the discontinuous deposit comprises a first and a second region, the islets present in the first and second regions differing in at least their colour and/or mean size and/or density.

In one implementation example, two different corrective compositions, especially of different colour, are present in the first and second regions.

The discontinuous deposit may also comprise a first and a second region, the islets present in the first and second regions differing at least in their colorimetric difference ΔE in the CIELab space, with the colour of all or part of the deposit of foundation composition. As a reminder, the ΔE is defined by the following relationship:

$$\Delta E^* = \sqrt{((L_1-L_2)^2 + (a_1-a_2)^2 + (b_1-b_2)^2}$$

in which:
$L_1, a_1, b_1$ are the coordinates in the colorimetric space of the first colour to be compared and $L_2, a_2, b_2$ are those of the second colour in the CIELab system (indices L luminance, a red, b yellow).

This measurement of the ΔE between a first region of the face comprising few or no islets and a second region of the face comprising more islets may be performed using a Chromasphere. The following protocol may be used: 100 mg of foundation are weighed out and applied with a bare finger onto the face; the corrective composition is then applied. After a drying time of 15 minutes, images of the made-up cheek, on a first region and on a second region, respectively, are acquired using the Chromasphere. The measurement difference corresponding to the ΔE reflects the desired heterogeneity.

Such variations in the appearance characteristics of the islets may advantageously make it possible to recreate natural effects.

It is advantageously possible to obtain a discontinuous deposit of islets in which a first region has an islet density greater than that of a second region and the first region is on the cheeks and the second region is in the periocular area or on the forehead.

In particular, it is possible to obtain a discontinuous deposit of islets in which a first region has an islet density greater than that of a second and of a third region and the first region is on the cheeks and the second and third regions are in the periocular area and on the forehead, respectively.

The islets obtained may have a colour difference ΔE in the CIELab space of greater than or equal to 1 and especially 3, with the colour of all or part of the deposit of foundation composition.

The discontinuous deposit may also be obtained by applying an electric and/or magnetic field and/or an excess pressure after the corrective composition has been applied to the surface to be made up, especially to the foundation deposit.

In this case, the intensity of the magnetic field applied in proximity may be between 1 mT and 2 T and the corrective composition may comprise particles of non-zero magnetic susceptibility, for example based on iron or rare-earth metals.

Removal and/or Movement of the Foundation Performed in Step b)

The removal and/or movement of the foundation performed in step b) preferably make it possible to form a discontinuous network of islets that locally modifies the appearance of the makeup so as to create the desired pattern.

The foundation may, during step b) be removed by being placed in contact with a surface that has a plurality of regions with different physicochemical properties.

In this case, the surface is, particularly preferably, placed in contact with the foundation deposit and removed relative thereto so as locally to remove the foundation and to obtain the pattern, and especially the desired discontinuous network of islets.

The surface particularly preferably comprises a plurality of regions with different retention properties for the foundation composition. The surface comprises, for example, a plurality of absorbent and/or adhesive zones, especially of deposits of absorbent and/or adhesive composition, making it possible to remove the foundation when they come into contact with it.

At least one of the following materials may be used as material constituting the adhesive zones: an oily and in particular thick deposit, optionally having a viscosity of between 2 Pa·s and 200 Pa·s, a polymer or material combining polymer and plasticizer whose Tg is less than 10° C. and optionally less than 4° C., and/or pressure-sensitive adhesives (PSA).

More particularly, as material constituting the adhesive zones, use may be made of elastomers, to which may be added a plasticizer or a solvent that is capable of lowering the Tg.

These elastomers may be acrylic or methacrylic polymers, or acrylic or methacrylic copolymers, sparingly crosslinked or non-crosslinked rubbers, or copolymers based on styrenes, butadiene, butylene and isoprene. In particular, use may be made of styrene-butadiene-styrene (SBS), styrene-ethylene/butylene-styrene (SEBS), styrene-ethylene/propylene (SEP) and styrene-isoprene-styrene (SIS).

The use of thick oils and of pressure-sensitive adhesives may be advantageous for removing material if the foundation is relatively dry or powdery. The term "relatively dry" means that the coating does not have an oily feel.

The absorbent zones preferably make it possible to remove the foundation by capillary action. It is possible, in this case, to use absorbent zones comprising, and especially consisting of, a fabric (assembly of fibres that take up foundation between the fibres), cardboard, a flocked support, one or more holes, or one or more alveoli.

The flocked support may comprise an assembly of fibres retained at one end. These fibres preferably have a diameter of between 2 and 200 μm and a length of between 0.2 mm and 5 mm.

These fibres may preferably comprise, and especially may consist of, a polymer, preferably polyamide, preferably polyamide 6-6 (Nylon®). A mixture of fibres of different sizes may be used, for example a mixture of fibres 200 μm and 10 μm in diameter.

When the absorbent zones comprise one or more holes or alveoli, the diameter and depth of these holes or alveoli may be between 0.3 mm and 5 mm.

The absorbent zones may also comprise reliefs, especially made of cardboard or elastomeric material with a Young's modulus of less than or equal to 100 MPa. These reliefs have, for example, a height of between 1 and 5 mm and a size, measured at the tip, of between 0.3 mm and 5 mm. The mean space between two adjacent reliefs may be between 0.1 mm and 1 mm.

It is also preferably possible to use absorbent zones that allow foundation to be taken up by a surface tension effect. In this case, the absorbent zone may have a high surface tension, for example greater than 40 mN/m.

The absorbent zone enabling foundation to be taken up by a surface tension effect may be made, for example, of metal, especially of iron, of metal oxide or ceramic, or of polymer, and its surface tension may be higher than that of the skin and higher than that of the foundation composition.

Zones having an absorbent nature by capillary action or surface tension may advantageously be relatively easy to wash after use.

As a variant, use may be made of absorbent fillers such as hydrophilic materials, for instance magnesia powder, or hollow materials, for instance pozzolana powder or a ceramic or sintered materials.

Oil-absorbent fillers that may especially be mentioned include:
  silica powders such as porous silica microspheres, polydimethylsiloxane-coated amorphous silica microspheres, silica silylate powders, especially those sold under the name Dow Corning VM-2270 Aerogel Fine Particles by the company Dow Corning and under the name Enova Aerogel MT 1100 by the company Cabot, amorphous hollow silica particles, and precipitated silica powders surface-treated with a mineral wax,
  acrylic polymer powders, such as: polymethyl methacrylate/ethylene glycol dimethacrylate porous spheres, ethylene glycol dimethacrylate/lauryl methacrylate copolymer powders,
  polyamide powders such as: Nylon-6 powder,
  perlite or magnesium carbonate powders,
  and mixtures thereof.

As a variant, the foundation is, during step b), taken up by suction.

In this case, a suction surface bearing holes may be placed close to, especially in contact with, the foundation deposit, and the foundation may, during step b), be taken up by suction through the said holes.

The suction is preferably performed with a suction device that generates a suction power of between 10 W and 1000 W and preferably between 20 and 200 W. However, a suction power of less than 10 W may be used, especially when the suction takes place on a zone of relatively small surface area, for example less than 4 $cm^2$.

Use will be made, for example, of an assembly with a turbine suction of abovementioned power.

The suction device may be equipped with a suction nozzle onto which is attached, for example by click-fastening, the suction surface bearing holes.

The suction surface may be in the form of an element in sheet form bearing holes. The area of the zone on which the holes are present (area of the holes included) is, for example, between 10 and 150 $cm^2$, for example between 50 and 80 $cm^2$.

The suction surface bearing holes comprises, for example, holes with a size of less than or equal to 2 mm, preferably less than 1 mm, for example with a size of between 300 μm and 500 μm. The suction surface bearing holes preferably comprises at least 50 holes, for example between 50 and 150 holes.

To perform the suction, the suction device and the suction surface bearing holes may be placed close to the foundation deposit and then, without moving, the suction is switched on for a few seconds.

It is particularly advantageous to use suction in order locally to take up a fluid, fatty or aqueous, or powdery foundation.

In one embodiment example, the foundation is, during step b), moved by being placed in contact with a plurality of reliefs borne by the surface of a tool.

These reliefs have, for example, a height of between 1 and 5 mm and a diameter, measured at the tip, of between 0.3 mm and 5 mm.

In one embodiment example, the foundation is, during step b), moved by spraying material.

To do this, use may be made of a spraying device that generates a spraying power of between 10 W and 1000 W and preferably between 20 and 200 W. However, a propulsion power of less than 10 W may be used, especially when the spraying takes place on a zone of relatively small surface area, for example less than 4 $cm^2$.

For example, a blower with a turbine or a fan of the abovementioned power is used.

The spraying device may be equipped with a spraying nozzle onto which is attached, for example by click-fastening, a surface bearing holes. This surface bearing holes may have the same characteristics as the suction surface bearing holes described above.

To perform the spraying, the spraying device and the surface bearing holes may be placed close to the foundation deposit and then, without moving, the spraying is switched on for a few seconds.

It is particularly advantageous to use the spraying of material in order locally to move a fluid, fatty or aqueous foundation, a foundation of emulsified formulation or a powdery foundation.

In this case, the foundation may be moved by a flow of gas, especially by spraying with compressed air.

As a variant, the foundation is moved by spraying a pulverulent composition and/or by spraying a liquid. In this case, a solvent that is capable of dissolving the foundation composition may be sprayed onto the foundation deposit.

As solvents that may be used for dissolving the foundation composition, mention may be made of: alkanes, especially hexane, isododecane or octane, silicones, especially PDMS, ether, acetone, ethanol, water, and mixtures thereof.

In one embodiment example, the foundation is, during step b), moved by applying an electromagnetic field, the foundation preferably comprising particles of non-zero magnetic susceptibility, and a magnetic field being applied close to the foundation deposit so as to move these particles. In this case, the foundation may comprise particles based on iron or on rare-earth metals, and the intensity of the applied magnetic field may be between 1 mTesla and 2 Tesla.

Discontinuous Network of Islets

As mentioned above, the removal and/or movement of the foundation performed in step b) preferably makes it possible to obtain a discontinuous network of islets.

The discontinuous network of islets may comprise islets that are touching and islets that are separate. As a variant, the discontinuous network of islets may consist of a set of separate islets.

The discontinuous network of islets preferably has all or some of the following characteristics:
a) the islets have a mean size of between 0.05 mm and 3 mm, preferably between 0.1 mm and 1.5 mm and particularly preferably between 0.3 mm and 0.9 mm, and/or
b) the mean distance separating two adjacent islets is between 0.25 mm and 20 mm, preferably between 0.5 mm and 5 mm and particularly preferably between 1.5 mm and 2.5 mm, and/or
c) the discontinuous network comprises at least 5, preferably at least 10, preferably at least 30 and particularly preferably at least 100 islets.

The size of an islet corresponds to its largest dimension.

The mean size of the islets corresponds to the arithmetic mean of the sizes of the said islets.

The distance between two islets corresponds to the distance separating the barycentres of the foundation zones covered with the said islets.

The mean distance between two adjacent islets corresponds to the arithmetic mean on the number of pairs of adjacent islets of the distances separating two adjacent islets.

The sizes of islets and distances separating two islets are, unless otherwise mentioned, measured just after the removal and/or movement of the foundation has been performed.

The density of islets in the discontinuous network is preferably greater than 5 islets per $cm^2$ of surface area of skin covered with the foundation, and less than 1000 per $cm^2$.

A discontinuous network of islets having:
islets with a mean size of between 0.4 and 4 mm,
a mean distance separating two adjacent islets of between 1 and 5 mm,
a number of islets greater than 1 per $cm^2$,
is preferably obtained so as to form a pattern that reproduces the appearance of freckles.

The islets are preferably formed according to a predefined pattern as detailed hereinbelow.

The appearance linked, for example, to freckles may advantageously be reproduced by creating a discontinuous network of islets having at least two regions within which the islets differ in at least one of their appearance characteristics.

Thus, the discontinuous network may comprise a first and a second region, the islets present in the first and second regions differing in at least their colour and/or mean size and/or density and/or shape and/or gloss.

Preferably, the discontinuous network comprises a first and a second region, the islets present in the first and second regions differing in at least their colour and/or mean size and/or density.

The discontinuous network may also comprise a first and a second region, the islets present in the first and second regions differing at least in their colorimetric difference ΔE in the CIELab space, with the colour of all or part of the deposit of foundation composition.

As a reminder, the ΔE is defined by the following relationship:

$$\Delta E^* = \sqrt{((L_1-L_2)^2 + (a_1-a_2)^2 + (b_1-b_2)^2}$$

in which:
$L_1$, $a_1$, $b_1$ are the coordinates in the colorimetric space of the first colour to be compared and $L_2$, $a_2$, $b_2$ are those of the second colour in the CIELab system (indices L luminance, a red, b yellow).

This measurement of the ΔE between a first region of the face comprising few or no islets and a second region of the face comprising more islets may be performed using a Chromasphere. The following protocol may be used: 100 mg of foundation are weighed out and applied with a bare finger onto the face; the foundation may then be moved and/or removed locally. After a drying time of 15 minutes, images of the made-up cheek, on a first region and on a second region, respectively, are acquired using the Chromasphere.

The measurement difference corresponding to the ΔE reflects the desired heterogeneity.

Such variations in the appearance characteristics of the islets may advantageously make it possible to recreate natural effects.

It is advantageously possible to obtain a discontinuous network of islets in which a first region has an islet density greater than that of a second region and the first region is on the cheeks and the second region is in the periocular area or on the forehead.

In particular, it is possible to obtain a discontinuous network of islets in which a first region has an islet density greater than that of a second and of a third region and the first region is on the cheeks and the second and third regions are in the periocular area and on the forehead, respectively.

The islets obtained may have a colour difference ΔE in the CIELab space of greater than or equal to 1 and especially 3, with the colour of all or part of the deposit of foundation composition.

Properties of the Cosmetic Device According to the Invention

As mentioned above, according to another of its aspects, the invention relates to a cosmetic device with a peripheral surface comprising islets arranged non-uniformly within a surrounding surface, the said islets each having a largest dimension of at least 0.8 mm and having a shape and/or properties for taking up and/or releasing a product present on the skin or in applying thereon a shape and/or properties different from those of the surrounding surface, so as to lead to the creation on the skin of a pattern whose appearance is linked to the arrangement of the islets on the peripheral surface.

The islets may be in relief and protrude relative to the surrounding surface. In this case, as will be detailed hereinbelow, the islets may, by being placed in contact with a makeup composition applied to the skin, make it possible locally to move the said makeup composition in order to obtain the desired pattern.

In this case, the release or uptake of product may originate from the affinity of this product for the islets.

In one embodiment example, the islets have physico-chemical properties that are distinct from those of the surrounding surface.

Preferably, the islets comprise, and especially consist of, adhesive and/or absorbent islets, especially of deposits of adhesive composition and/or of absorbent composition.

At least one of the following products may be used as adhesive composition: an oily and in particular thick deposit, optionally having a viscosity of between 2 Pa·s and 200 Pa·s, a polymer or material combining polymer and plasticizer whose Tg is less than 10° C. and optionally less than 4° C., and/or pressure-sensitive adhesives (PSA).

More particularly, as material constituting the deposits of adhesive composition, use may be made of elastomers, to which may be added a plasticizer or a solvent that is capable of lowering the Tg.

These elastomers may be acrylic or methacrylic polymers, or acrylic or methacrylic copolymers, sparingly crosslinked or non-crosslinked rubbers, or copolymers based on styrenes, butadiene, butylene and isoprene. In particular, use may be made of styrene-butadiene-styrene (SBS), styrene-ethylene/butylene-styrene (SEBS), styrene-ethylene/propylene (SEP) and styrene-isoprene-styrene (SIS).

The use of thick oils and of pressure-sensitive adhesives may be advantageous for removing material if the foundation is relatively dry or powdery. The term "relatively dry" means that the coating does not have an oily feel.

The deposits of absorbent composition preferably make it possible to remove the foundation by capillary action. It is possible, in this case, to use absorbent compositions comprising, and especially consisting of, a fabric (assembly of fibres that take up foundation between the fibres), cardboard, or a flocked support. It is also possible locally to absorb foundation by using absorbent islets in the form of one or more holes or one or more alveoli.

The flocked support may comprise an assembly of fibres retained at one end. These fibres preferably have a diameter of between 2 and 200 µm and a length of between 0.2 mm and 5 mm.

These fibres may preferably comprise, and especially may consist of, a polymer, preferably polyamide, preferably polyamide 6-6 (Nylon®). A mixture of fibres of different sizes may be used, for example a mixture of fibres 200 µm and 10 µm in diameter.

When the absorbent islets comprise one or more holes or alveoli, the diameter and depth of these holes or alveoli may be between 0.3 mm and 5 mm.

The deposits of absorbing composition may also comprise reliefs, especially made of cardboard or elastomeric material with a Young's modulus of less than or equal to 100 MPa. These reliefs have, for example, a height of between 1 and 5 mm and a size, measured at the tip, of between 0.3 mm and 5 mm. The mean space between two adjacent reliefs may be between 0.1 mm and 1 mm.

It is also preferably possible to use absorbent islets that allow foundation to be taken up by a surface tension effect. In this case, the absorbent islets may have a high surface tension, for example greater than 40 mN/m.

The absorbent islets enabling foundation to be taken up by a surface tension effect may be made, for example, of metal, especially of iron, of metal oxide or ceramic, or of polymer, and their surface tension may be higher than that of the skin and higher than that of the foundation composition.

Islets having an absorbent nature by capillary action or surface tension may advantageously be relatively easy to wash after use.

As a variant, use may be made of absorbent fillers such as hydrophilic materials, for instance magnesia powder, or hollow materials, for instance pozzolana powder or a ceramic or sintered materials.

Oil-absorbent fillers that may especially be mentioned include:

- silica powders such as porous silica microspheres, polydimethylsiloxane-coated amorphous silica microspheres, silica silylate powders, especially those sold under the name Dow Corning VM-2270 Aerogel Fine Particles by the company Dow Corning and under the name Enova Aerogel MT 1100 by the company Cabot, amorphous hollow silica particles, and precipitated silica powders surface-treated with a mineral wax,
- acrylic polymer powders, such as: polymethyl methacrylate/ethylene glycol dimethacrylate porous spheres, ethylene glycol dimethacrylate/lauryl methacrylate copolymer powders,
- polyamide powders such as: Nylon-6 powder,
- perlite or magnesium carbonate powders,
- and mixtures thereof.

In one preferred variant, the hydrophilicity of the islets may be different from that of the surrounding surface.

Thus, the islets may be configured to allow the removal of a product, especially a foundation, applied to the skin during their placing in contact therewith. This removal of product advantageously makes it possible to obtain the desired pattern.

The islets may be defined with the aid of pins that can be moved relative to the surrounding surface. These pins are defined, for example, by electrically controlled actuators.

The use of pins that can be moved relative to the surrounding surface advantageously makes it possible to modify the distribution of the islets. In the context of the invention, the user can thus personalize the arrangement of the islets in the device so as to obtain on his skin the pattern of his choice, for example a particular desired skin grain and/or freckles.

In one implementation example, the islets may be defined by grains of a product that can transfer onto the skin and/or by a liquid. In this case, the product may advantageously be coloured. The liquid may make it possible to take up on the peripheral surface a product that is then transferred onto the skin. As a variant, the liquid is transferred onto the skin, the liquid in this case preferably being coloured.

The device may comprise islets having a largest dimension of greater than or equal to 2 mm and/or islets having a largest dimension of greater than or equal to 3 mm.

The device may comprise islets having a largest dimension of between 0.8 and 2 mm, islets having a largest dimension of between 2 mm (limit excluded) and 3 mm and also islets having a largest dimension of between 3 mm (limit excluded) and also 5 mm.

The number of islets having a largest dimension of between 0.8 and 2 mm may be greater than the number of islets having a largest dimension of between 2 (limit excluded) and 3 mm and than the number of islets having a largest dimension of between 3 (limit excluded) and 5 mm.

The device may comprise islets of circular contour and/or islets of non-circular contour. The device may comprise islets that are touching and islets that are separate.

The device may comprise islets of circular contour in a greater number than that of the islets of non-circular contour.

The device may comprise adjacent islets whose spacing is greater than or equal to 2 mm.

Discontinuous Network of Visible Zones

As mentioned hereinabove, the use of the device according to the invention may advantageously make it possible to obtain a discontinuous network of visible zones.

The discontinuous network of visible zones preferably has all or some of the following characteristics:

a) the visible zones have a mean size of between 0.05 mm and 3 mm, preferably between 0.1 mm and 1.5 mm and particularly preferably between 0.3 mm and 0.9 mm, and/or b) the mean distance separating two adjacent visible zones is between 0.25 mm and 20 mm, preferably between 0.5 mm and 5 mm and particularly preferably between 1.5 mm and 2.5 mm, and/or c) the discontinuous network comprises at least 5, preferably at least 10, preferably at least 30 and particularly preferably at least 100 visible zones.

The size of a visible zone corresponds to its largest dimension.

The mean size of the visible zones corresponds to the arithmetic mean of the sizes of the said visible zones.

The distance between two visible zones corresponds to the distance separating the barycentres of the said visible zones.

In the particular case of the formation of visible zones by removal and/or movement of foundation present on the skin, the distance between two visible zones corresponds to the distance separating the barycentres of the zones of foundation covered by the said visible zones.

The mean distance between two adjacent visible zones corresponds to the arithmetic mean on the number of pairs of adjacent visible zones of the distances separating two adjacent visible zones.

The sizes of the visible zones and distances separating two visible zones are, unless otherwise mentioned, measured just after the end of use of the device according to the invention.

The density of visible zones in the discontinuous network is preferably greater than 5 visible zones per $cm^2$ of surface area of treated skin, and less than 1000 per $cm^2$.

A discontinuous network of visible zones having:

- visible zones with a mean size of between 0.4 mm and 4 mm,
- a mean distance separating two adjacent visible zones of between 1 mm and 5 mm,
- a number of visible zones greater than 1 per $cm^2$, is preferably obtained so as to form a pattern that reproduces the appearance of freckles.

The appearance linked, for example, to freckles may advantageously be reproduced by creating a discontinuous network of visible zones having at least two regions within which the visible zones differ in at least one of their appearance characteristics.

Thus, the discontinuous network may comprise a first and a second region, the visible zones present in the first and second regions differing in at least their colour and/or mean size and/or density and/or shape and/or gloss.

Preferably, the discontinuous network comprises a first and a second region, the visible zones present in the first and second regions differing in at least their colour and/or mean size and/or density.

The discontinuous network may also comprise a first and a second region, the visible zones present in the first and second regions differing at least in their colorimetric difference ΔE in the CIELab space, with the colour of all or part of the deposit of foundation composition.

As a reminder, the ΔE is defined by the following relationship:

$$\Delta E^* = \sqrt{((L_1-L_2)^2+(a_1-a_2)^2+(b_1-b_2)^2}$$

in which:

$L_1$, $a_1$, $b_1$ are the coordinates in the colorimetric space of the first colour to be compared and $L_2$, $a_2$, $b_2$ are those of the second colour in the CIELab system (indices L luminance, a red, b yellow).

This measurement of the ΔE between a first region of the face comprising few or no visible zones and a second region of the face comprising more visible zones may be performed using a Chromasphere. The following protocol may be used: 100 mg of foundation are weighed out and applied with a bare finger onto the face; a discontinuous network of visible zones is then created by performing a process according to the invention. After a drying time of 15 minutes, images of the made-up cheek, on a first region and on a second region, respectively, are acquired using the Chromasphere.

The measurement difference corresponding to the ΔE reflects the desired heterogeneity.

Such variations in the appearance characteristics of the visible zones may advantageously make it possible to recreate natural effects.

It is advantageously possible to obtain a discontinuous network of visible zones in which a first region has a visible zones density greater than that of a second region and the first region is on the cheeks and the second region is in the periocular area or on the forehead.

In particular, it is possible to obtain a discontinuous network of visible zones in which a first region has a visible zones density greater than that of a second and of a third region and the first region is on the cheeks and the second and third regions are in the periocular area and on the forehead, respectively.

The visible zones obtained may have a colour difference ΔE in the CIELab space of greater than or equal to 1 and especially 3, with the colour of all or part of the deposit of foundation composition.

DESCRIPTION OF THE FIGURES

The invention may be understood more clearly on examining the attached drawing, in which:

FIGS. 6 and 7 show applicators that may be used in the context of the processes according to the invention, FIG. 8 is a representation of the developed surface of an application surface of an applicator that may be used in the context of the processes according to the invention, FIGS. 9A and 9B are diagrammatic and partial cross sections of an embodiment example of an application surface of an applicator that may be used in the context of the invention, FIGS. 12, 13, 14a and 15 to 21 illustrate variants of makeup processes according to the invention.

Figure 1:
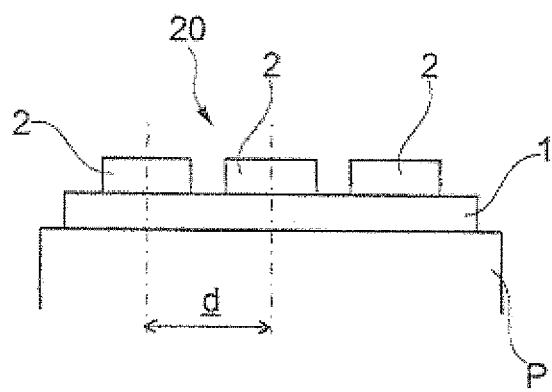
FIG. 1 shows diagrammatically in cross section a skin made up via a process according to the invention.

In the drawings, the real proportions have not necessarily been respected out of concern for the clarity of the drawing.

FIG. 1 shows the makeup result on a skin P obtained after a process according to the invention.

The skin P is first coated with a foundation composition 1, this deposit 1 possibly being, as illustrated, continuous (i.e. integral) or, as a variant, distributed discontinuously on the surface of the treated skin P.

The foundation 1 may be fluid or pulverulent and, for example, may be applied by finger or by using an applicator (sprayer, sponge, aerograph, etc.).

In a second stage, the user applies the corrective composition so as to form a discontinuous deposit 20 of islets 2 of corrective composition on the skin P.

In one embodiment example, the user applies, in a second stage, a makeup product so as to form a discontinuous network 20 of visible zones 2 on the skin P.

This application is performed, for example, by means of the devices described in FIGS. 6 and 7.

The islets 2 are, in the discontinuous deposit 20, separated by a distance d connecting the barycentres of the islets concerned. The mean distance (arithmetic mean over the number of adjacent pairs of islets 2 constituting the discontinuous deposit 20) separating two adjacent islets 2 is, for example, between 0.5 and 5 mm.

When a discontinuous network of visible zones is formed, adjacent visible zones 2 are, in the discontinuous network 20, separated by a distance d connecting the barycentres of the visible zones concerned. The mean distance (arithmetic mean over the number of adjacent pairs of visible zones 2 constituting the discontinuous network 20) separating two adjacent visible zones 2 is, for example, between 0.5 and 5 mm.

Figure 2:
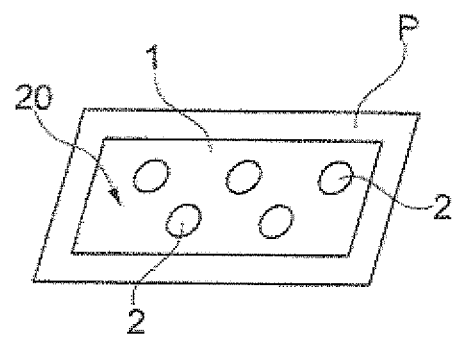
FIG. 2 shows in top view the made-up surface of FIG. 1, FIGS. 1A to 1D and 3 to 5 show examples of made-up surfaces according to the invention.

FIG. 2 shows a top view of FIG. 1. The islets 2 or visible zones 2 may have different shapes, some islets 2 or visible zones 2 having, for example, a circular shape and other islets 2 or visible zones 2 having an oblong and especially elliptical shape.

As a variant, all of the islets 2 or visible zones 2 constituting the discontinuous deposit 20 or the discontinuous network 20 may have substantially the same shape.

Figure 3:
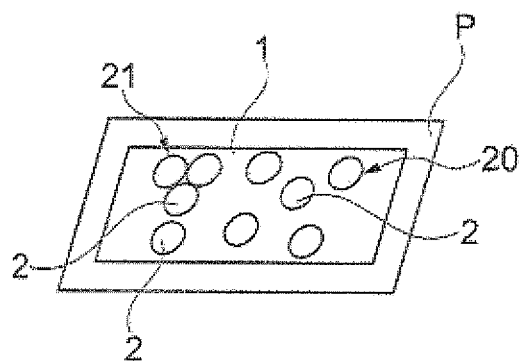

FIG. 3 shows a variant in which the discontinuous deposit 20 of islets 2 of corrective composition comprises islets 2 that are touching, thus forming an aggregate 21 of islets 2, and islets 2 that are separate.

FIG. 3 may also represent a variant in which the discontinuous network 20 of visible zones 2 comprises visible zones 2 that are touching, thus forming an aggregate 21 of visible zones 2, and visible zones 2 that are separate.

Figure 4:
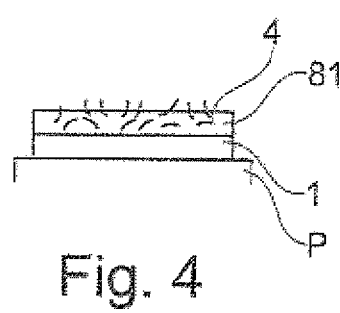

FIG. 4 is a cross section of a surface of skin P made up according to the invention, covered with a foundation deposit 1 that is covered with a continuous deposit of a product 81, especially of corrective composition 81 comprising visible substances 4. The visible substances 4 may give the product an inhomogeneous appearance.

In a variant not shown, the product, especially the corrective composition 81, comprising the visible substances 4, is deposited discontinuously on the foundation deposit 1.

In a variant not shown, the product, especially the corrective composition, is deposited on only part of the foundation deposit.

The visible substances 4 advantageously make it possible to create relief heterogeneities, rendering, for example, the appearance of the made-up surface more natural.

The visible substances 4 have been shown as being fibres; as a variant, other types of particles such as separate grains or agglomerates of grains may be used.

Figure 5:
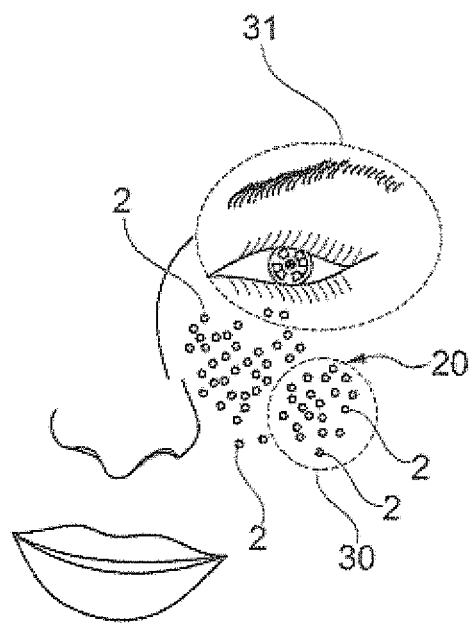

FIG. 5 shows a makeup result according to the invention, in which the discontinuous deposit 20 of islets 2 comprises a first region 30 and a second region 31. The discontinuous deposit 20 obtained after the makeup processes according to the invention may comprise at least 10 and preferably at least 30 islets 2.

The first region 30 is, as illustrated, located on a cheek and the second region 31 is located in the periocular area.

The makeup according to the invention shown in FIG. 5 shows that the density of the islets 2 present in the first region 30 is greater than the density of the islets 2 present in the second region 31.

The density of the islets 2 present in the first region 30 is, for example, greater than or equal to twice and especially five times the density of the islets 2 present in the second region 31.

First and second regions may be created, the islets of which differ from each other by other characteristics, for instance their colour, mean size, shape and/or gloss.

In a variant not shown, the first region 30 is on the cheeks and the second region 31 is on the forehead.

In one embodiment example, FIG. 5 shows a makeup result according to the invention, in which the discontinuous network 20 of visible zones 2 comprises a first region 30 and a second region 31. The discontinuous network 20 obtained after the makeup processes according to the invention may comprise at least 10 and preferably at least 30 visible zones 2.

The first region 30 is, as illustrated, located on a cheek and the second region 31 is located in the periocular area.

The makeup according to the invention shown in FIG. 5 shows that the density of the visible zones 2 present in the first region 30 is greater than the density of the visible zones 2 present in the second region 31.

The density of the visible zones 2 present in the first region 30 is, for example, greater than or equal to twice and especially five times the density of the visible zones 2 present in the second region 31.

First and second regions may be created, the visible zones of which differ from each other by other characteristics, for instance their colour, mean size, shape and/or gloss.

In a variant not shown, the first region 30 is on the cheeks and the second region 31 is on the forehead.

Figure 1A:
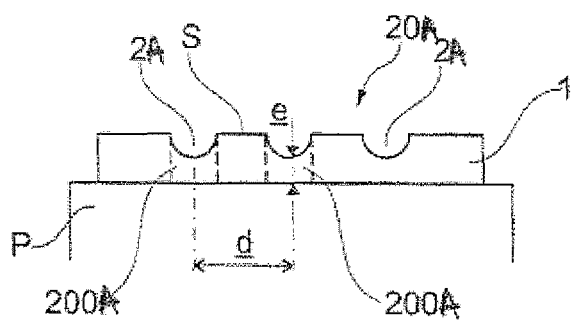

FIG. 1A shows the makeup result on a skin P obtained after a variant of a process according to the invention.

The skin P is first coated with a foundation composition 1, this deposit 1 possibly being, as illustrated, continuous (i.e. integral) or, as a variant, distributed discontinuously on the surface of the treated skin P.

The foundation 1 may be fluid or pulverulent and, for example, may be applied by finger or by using an applicator (sprayer, sponge, aerograph, etc.).

In a second stage, the user removes the foundation locally so as to form a discontinuous network 20A of islets 2A or of visible zones 2A on the skin P.

It is possible, as illustrated, to obtain a modification of the shape of the free surface S of the foundation deposit 1 due to islets 2A or visible zones 2A in the form of hollows resulting in a local decrease in the thickness e of the foundation deposit 1.

The hollows may be obtained by placing the foundation 1 in contact with an adhesive surface or by suction as will be detailed hereinbelow.

The islets 2A are, in the discontinuous network 20A, separated by a distance d connecting the barycentres of the zones 200A of foundation that are covered with the islets concerned. The mean distance (arithmetic mean over the number of adjacent pairs of islets 2A constituting the discontinuous deposit 20A) separating two adjacent islets 2A is, for example, between 0.5 and 5 mm.

As a variant, the adjacent visible zones 2A are, in the discontinuous network 20A, separated by a distance d connecting the barycentres of the zones 200 of foundation that are covered with the visible zones concerned. The mean distance (arithmetic mean over the number of adjacent pairs of visible zones 2A constituting the discontinuous network 20A) separating two adjacent visible zones 2A is, for example, between 0.5 and 5 mm.

Figure 1C:
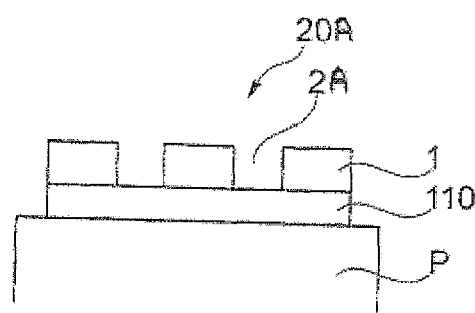
Figure 1B:
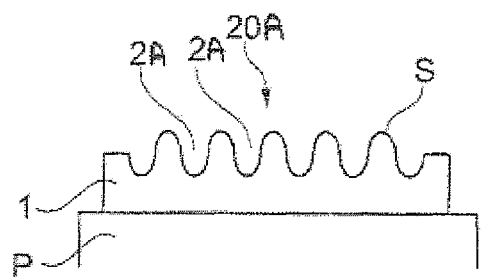

FIG. 1B shows a variant in which the removal and/or movement of the foundation performed in step b) has resulted in the production of a free surface S of the foundation deposit 1 comprising reliefs such as hollows and/or bumps. As illustrated, the free surface S comprises a succession of hollows and bumps, thus constituting the discontinuous network 20A of islets 2A or a discontinuous network 20A of visible zones 2A.

FIG. 1C shows an example of makeup according to the invention in which a coat 110 of coloured makeup composition has been applied to the skin before application of the foundation composition 1.

Once the coat of foundation composition 1 has been applied, it is possible by local removal of foundation 1 to form, in the foundation composition 1, islets 2A or visible zones 2A free of foundation.

Such a removal may be performed by means of the device of FIG. 6, whose pins 42 consist of an absorbent material.

In a variant not shown, the processes according to the invention make it possible locally, in the foundation composition 1, to lead to the formation of islets or visible zones in the form of hollows as illustrated in FIG. 1A.

The hollows or islets of zones free of foundation advantageously make it possible locally to modify the coverage of the foundation coat and thus to modify the appearance of the made-up surface due to the presence of the underlying coat of coloured makeup.

Figure 1D:
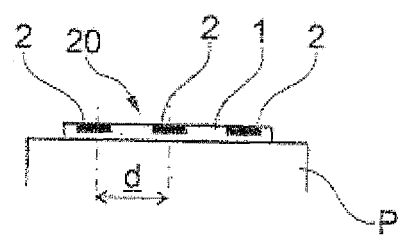

FIG. 1D shows a makeup result according to the invention in which a chemical reagent present on the pins 42 of the device of FIGS. 6 and 7 has been applied to a foundation deposit 1.

The applied chemical reagent can react with a compound present in the foundation so as to enable the foundation deposit 1 to change colour locally in order to form the discontinuous network 20 of visible zones 2.

The adjacent visible zones 2 are, in the discontinuous network 20, separated by a distance d connecting the barycentres of the visible zones concerned. The mean distance (arithmetic mean over the number of adjacent pairs of visible zones 2 constituting the discontinuous network 20) separating two adjacent visible zones 2 is, for example, between 0.5 and 5 mm.

FIG. 6 shows the device 40 for forming a pattern, and especially a discontinuous network of visible zones or a discontinuous deposit 20 of islets 2, in the context of the processes according to the invention. In the present text, reference will be made indiscriminantly to the device 40 or the applicator 40 when the device 40 is used for applying a product to keratin materials optionally bearing makeup.

The device 40 comprises a peripheral surface 41 comprising islets in the form of pins 42 intended to come into contact with a user's skin or, as a variant, with a foundation deposit present thereon. The device 40 is configured such that, during its movement over the keratin materials, a rotational movement relative to the axis X is imposed in the peripheral surface 41. In the present text, reference will be made indiscriminantly to the peripheral surface 41 or the applicator surface 41 when the device 40 is used for applying a product to keratin materials optionally bearing makeup.

In one embodiment example, the pins 42 bear a product to be applied to the skin (not shown) and the rotation of the peripheral surface 41 in contact with the made-up keratin materials makes it possible to produce by transfer a discontinuous network of visible zones.

In one embodiment example, the pins 42 bear a product to be applied to the skin (not shown) and the rotation of the peripheral surface 41 in contact with the made-up keratin materials makes it possible to produce by transfer the discontinuous deposit of islets of corrective composition.

In one embodiment example, the pins 42 consist of an absorbent material based on Nylon® flocking comprising a mixture of fibres 200 µm and 10 µm in diameter bonded together on a support. The pins 42 make it possible, in this case, during their contact with the foundation composition, locally to remove foundation so as to obtain the discontinuous network of islets or the discontinuous network of visible zones.

As a variant, the pins make it possible to move the foundation during their contact therewith so as to obtain the pattern, and especially the desired discontinuous network of islets or of visible zones.

In one embodiment example, the pins 42 bear a chemical reagent (not shown) that enables the foundation to change colour, for example dihydroxyacetone, and the rotation of the peripheral surface 41 in contact with the made-up keratin materials allows the said chemical reagent to be transferred so as to obtain the discontinuous network of visible zones. In this case, the foundation comprises an amine that can react with dihydroxyacetone so as to produce the colour change.

An example of a method for manufacturing a device 40 bearing pins 42 which can be used in the context of the processes according to the invention will now be described.

FIG. 8 shows a representation of a developed surface of a peripheral surface 41. As illustrated, the peripheral surface 41 comprises islets of circular contour and islets of non-circular contour. This peripheral surface 41 also comprises islets that are touching and islets that are separate.

This developed surface has, for example, dimensions of 30×20 mm.

Starting from the pattern shown in FIG. 8, a 3D file is produced in. STL format using the Solidworks® software. The axes x and y, in this file, are shown in FIG. 8 and the z coordinates are at −2 mm for the coloured zones and 0 mm for the white zones.

Next, starting with this file, an object that will serve as a mould is made, for example, using a 3D printer (Objet 30 from the company Objet Geometries Ltd).

A crosslinkable silicone (Silflo) is deposited on the mould such that all the surface is covered with a thickness of about 2 mm.

After setting to a solid, it is removed. The silicone is then bonded onto a roller about 1 cm in diameter.

The roller is equipped with a handle and a rotational axle, allowing the roller to be rolled without any appreciable friction.

The roller thus obtained can then be placed in contact with a pad delivering an adhesive so as to obtain a deposit which has adhesive zones selectively at its pins. These adhesive zones can allow the removal of foundation by placing the device in contact with a foundation deposit applied to the skin so as to obtain a discontinuous network of islets.

FIG. 7 shows an embodiment variant of a device 40 that may be used in the context of the processes according to the invention, comprising a reservoir 43 comprising a product, especially the corrective composition, intended to be applied onto a foundation deposit present on the skin and arranged to distribute this deposit on the pins 42 of the application surface 41 gradually as the applicator 40 moves in contact with the made-up keratin materials.

The application of the product makes it possible, for example, locally to move the foundation present on the skin so as to form the pattern, and preferably the desired discontinuous network of visible zones.

The reservoir 43 comprises, for example, calcium chloride particles, and is arranged to distribute them on the pins 42 of the surface 41 gradually as the device 40 moves in contact with the made-up keratin materials. Once applied by the device 40 to the foundation deposit, these particles can locally move the foundation so as to produce the desired pattern and especially the discontinuous network of islets.

In one embodiment example not shown, the pins are configured so as to create a discontinuous deposit of islets of corrective composition in shaded colours during the movement of the device. In other words, the pattern obtained by using the device produces an optical effect whose intensity varies strictly monotonously on moving along all or part of the path taken by the device.

It is also possible to use a device in plate form bearing pins and/or absorbent zones and/or holes.

In one embodiment example, the pins 42 can move relative to the peripheral surface. The pins 42 can be moved by hand, by a magnetic force or by an electromechanical force, depending on the systems used. The pins 42 may be mobile along the peripheral surface 41 and/or may be extended or retracted so as to create reliefs on the said peripheral surface.

In the latter case, the pins 42 may be covered with a fine and elastic surface. Thus, when the pins are extended, bumps emerge on the elastic surface. FIG. 9A shows the peripheral surface 41 comprising the pins in the retracted state, and FIG. 9B shows the peripheral surface 41 comprising the pins 42 emerging after application of an electromechanical force, for example.

The roller may then serve to take up the corrective composition and then, by transfer, to deliver it onto the skin by simple pressure.

In one particular case, an electro-sensitive surface is used (dielectric silicone used in the actuators) in an array such that this surface contains a drop of liquid, for example of an oil.

A plate is produced made of elastomer bearing several of these arrays, each being about 2 mm in size and 2 mm away from its neighbour. Each array is electrically connected to an electric generator delivering about 500 V. It is possible to choose the arrays that will be electrically charged so as to obtain the desired pattern and, in particular, to choose to obtain a random array.

When the electric charge is delivered, the electro-sensitive surface of each driven array retracts and thus presses the liquid and, consequently, brings about swelling of the array. The arrays that have not been electrically driven keep their initial flat shape.

Such an array is described in the publication "Millimetre-scale bubble-like dielectric elastomer actuators" by Carpi et al., Polymer International (2009), Volume: 59, Issue: 3, Pages: 407-414.

This array may be fixed, for example by click-fastening, onto different types of surfaces (rollers, sponges, pads or surfaces having a shape matching a part of the body) so as to form a cosmetic device that can be used in the context of the present invention.

This assembly may then serve to take up the corrective composition and then, by transfer, to deliver it onto the skin by simple pressure.

It is understood that, in accordance with a variant not shown, the device may have a peripheral surface equipped with a plurality of holes instead of the pins 42, a product, especially the corrective composition, being distributed through these holes so as to obtain the pattern, and especially the desired discontinuous deposit of islets of corrective composition or discontinuous network of visible zones.

In this embodiment example, an alveolar material, such as a polyurethane foam, may be used. Thus, a foam roller can be made and then part of its surface covered with an impermeable layer bearing holes, for instance a smooth plastic handle bearing holes.

Since the handle has holes, product will be transferred at these holes, especially corrective composition, when the roller is pressed on the skin.

According to another variant not shown, the device comprises, instead of the pins 42, a plurality of regions that differ especially by their hydrophilicity. In the latter embodiment example, the corrective composition is selectively present, before application to the made-up surface, at the most hydrophilic regions so as to form the discontinuous deposit of islets when it is applied.

The corrective composition may also be selectively placed at the hydrophobic regions. In such an embodiment example, as in the case of offset printing, the hydrophilic regions may be made of aluminium and the hydrophobic regions may be made of copper or a silicone polymer.

An ink comprising a mixture of water and coloured molecules may then be placed on the peripheral surface of the device. The difference in surface tension forces the water to position itself at the hydrophilic regions and the coloured molecules at the hydrophobic regions.

Next, by simple transfer, with or without drying beforehand, the pattern will be able to be relayed onto the skin.

A device that may or may not be uniformly covered with a dyestuff that is non-transferable or sparingly transferable when it is dry may also be used. After wetting the said dyestuff with a suitable solvent, especially with water, a product, especially a corrective composition, which can be transferred onto the made-up keratin materials is obtained.

Thus, by depositing a solvent in a certain pattern, it is possible to reproduce the said pattern via transfer onto the skin by depositing a product, especially the corrective composition.

It is also possible to use a device with a peripheral surface of non-uniform roughness or absorbent nature. This example uses two surfaces, one of which is quite smooth and the other markedly rougher or more absorbent.

For example, a viscous solution of PSA adhesive polymer is deposited on a roller, in small zones. Next, the roller is passed over a powder of small fibres (2 mm long, 20 µm in diameter). Only the adhesive zones retain the fibres.

When the roller thus treated is placed in contact with a product to be applied, especially the corrective composition, the zones bearing small fibres accumulate a large amount of the said products, especially of corrective composition, which may be delivered by simple pressure onto the skin.

It is also possible to use a device whose smooth peripheral surface bears discontinuous islets of a product that can transfer onto the skin, especially of corrective composition. The peripheral surface may be made of a sparingly adherent material, such as PTFE.

The adhesion of the product, especially the corrective composition, to the peripheral surface is sufficient for the roller to be able to be manipulated.

On contact with the skin, the product, especially the corrective composition, is transferred, leaving the roller with less or no product.

In one embodiment example, the islets of product, especially of corrective composition, borne by the peripheral surface are formed of dry material that is optionally adhesive on at least one of its faces.

On contact with the made-up surface, the adhesion force that is created exceeds the adhesion of the product, especially of the corrective composition, to the device, thus bringing about transfer.

In another embodiment example, the product, especially the corrective composition, is formed from small fibres (typically 1 mm long by 10 µm in diameter).

The small fibres are maintained at the peripheral surface of the device by means of electrostatic attraction and/or by the presence of a fluid and/or an adhesive material. It is understood that the device 40 may, in accordance with a variant not shown, have a surface 41 bearing pins 42, the said pins comprising or consisting of deposits of an adhesive composition. In this case, on contact of the device 40 with the foundation deposit, this deposit may be locally removed by the adhesive so as to form the discontinuous network of islets.

When the device comprises a plurality of adhesive zones, the adhesive nature may be restored before each use by contact on a pad that delivers adhesive, especially in a predefined pattern. As a variant, the adhesive nature may be restored after cleaning, for example by eliminating the foundation composition previously taken up.

In an embodiment example not shown, the pins are configured so as to take up the foundation composition in graded shades during the movement of the device. In other words, the pattern obtained by taking up foundation produces an optical effect whose intensity varies strictly monotonously on moving along all or part of the path taken by the device.

It is understood that, in accordance with a variant not shown, the device 40 may have a suction surface 41 equipped with a plurality of holes instead of the pins 42, the foundation being able to be taken up by suction through the said holes when the device 40 is close to, for example in contact with, the foundation deposit. Suction of the foundation through the holes may make it possible to obtain the desired pattern, and especially the desired discontinuous network of visible zones. In this case, the device may be fixed or mobile relative to the foundation deposit.

According to another variant not shown, the device 40 comprises, instead of the pins 42, a plurality of regions that differ especially by their hydrophilicity, for example a plurality of islets whose hydrophilicity is different from that of the neighbouring surface surrounding them.

In the latter embodiment example, the foundation may be selectively taken up at the most hydrophilic regions so as to obtain the desired pattern, and especially the desired discontinuous network of islets.

As a variant, the product may be selectively present, before application to the made-up surface, on the most hydrophilic regions so as to form the desired pattern during its application.

As a variant, the foundation may be selectively taken up at the most hydrophobic regions so as to obtain the desired pattern, and especially the desired discontinuous network of islets.

The product may also be selectively placed at the hydrophobic regions.

In this case, as in the case of offset printing, the hydrophilic regions may be made of aluminium and the hydrophobic regions may be made of copper or a silicone polymer.

It is also possible to use a device with a surface of non-uniform roughness or absorbent nature. This example uses two surfaces, one of which is quite smooth and the other markedly rougher or more absorbent.

For example, a viscous solution of PSA adhesive polymer is deposited on a roller, in small zones. Next, the roller is passed over a powder of small fibres (2 mm long, 20 µm in diameter). Only the adhesive zones retain the fibres.

When the roller thus treated is placed in contact with a foundation deposit, the zones bearing the small fibres take up a large amount of foundation.

As a function of the arrangement of the adhesive zones and thus of the fibres, the pattern, and especially the arrangement of the network of discontinuous islets, formed on the made-up surface can be imposed.

It is also possible to use a device in the form of a plate bearing a plurality of absorbent zones allowing the foundation to be taken up so as to obtain the desired pattern.

It is also possible to use a device in the form of a plate bearing a plurality of holes through which the foundation can be sucked so as to obtain the desired pattern.

It is also possible to use a device in the form of a plate bearing a plurality of pins that make it possible to move the foundation when the device is placed in contact with the foundation, the said movement making it possible to obtain the desired pattern.

Use may be made of sandpaper or a brush enabling the foundation, by local contact therewith, to be taken up so as to form the desired pattern.

The user can place the device in contact non-uniformly with the foundation deposit so as to obtain the discontinuous network of islets.

Needless to say, droplets that locally modify the form of the free surface may be sprayed through holes in order to obtain the desired pattern, and especially the desired discontinuous network of islets.

It is also possible to use applicators of "pad" type with mobile ends that can change their arrangement randomly. This principle is based on a guide membrane bearing holes, which may be flexible or hard. Small stems are placed in each of the holes. The length of the stems is greater than the thickness of the guide membrane. The system is equipped with a means for preventing the stems from coming out of the hole, without preventing the stems from moving. For example, another membrane that blocks off the exit of the stems may be placed on the rear face, or alternatively each stem is retained by an elastic zone, or alternatively each stem has one or two stubs that limit the movement beyond a certain course. The mobile stems may be moved individually or in a group by simple mechanical pressure, by hydraulic pressure or by electromagnetic or electrostatic force. A system may make it possible to block the stems so that they do not move during the application. This system may use a mechanical force, an electromagnetic force or an electrostatic force, the presence of frictions being such that the force on application is not sufficient to move the stems, or a braking system that is deactivated to move the stems and is activated to block them. Finally, a last flexible membrane may be added above the group of stems. In this case, the stems do not come into contact with the skin and push the flexible membrane, then giving it reliefs by pressure.

For example, the guide membrane has a thickness of between 1 mm and 1 cm. The stems have, for example, a length of between 2 mm and 2 cm. The diameters of the stems are, for example, between 0.3 and 5 mm. The stems may or may not have a circular cross section.

Figure 10:
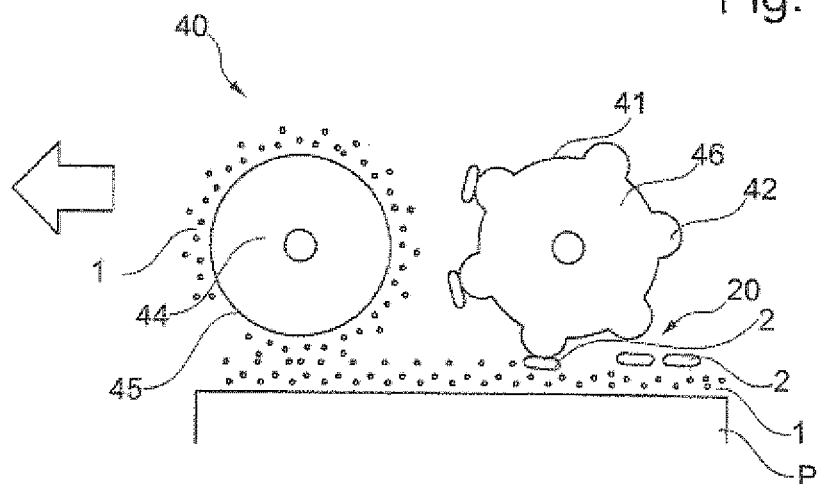
FIG. 10 is a diagrammatic and partial cross section of an embodiment example of an applicator according to the invention.

FIG. 10 shows a variant of the applicator 40 for applying the foundation composition 1 and the discontinuous deposit of islets 2 in a single application action.

The applicator 40 is moved relative to the surface of skin P to be treated and comprises a first roller 44 comprising on its application surface 45 a coat of powdered foundation 1. The first roller ensures the application of the foundation 1 onto the skin P when it is moved relative to the skin P.

The applicator 40 also comprises a second roller 46 comprising pins 42 on its application surface 41. These pins bear, as illustrated, islets 2 of corrective composition and make it possible to obtain the discontinuous deposit 20 of islets 2 on the foundation coat 1 gradually as the applicator 40 is moved relative to the skin P.

The device 40 of FIG. 10 may also make it possible to apply the foundation composition 1 and to form a discontinuous network 20 of visible zones 2 in a single application action.

The device 40 is moved relative to the surface of skin P to be treated and comprises a first roller 44 comprising on its application surface 45 a coat of powdered foundation 1. The first roller ensures the application of the foundation 1 onto the skin P when it is moved relative to the skin P.

The device 40 also comprises a second roller 46 comprising pins 42 on its peripheral surface 41. These pins bear, as illustrated, deposits 2 of a product and make it possible to obtain a discontinuous network 20 of visible zones 2 on the foundation coat 1 gradually as the device 40 is moved relative to the skin P.

Needless to say, in a variant not shown, the device may comprise pins formed from absorbent zones making it possible locally to take up the foundation composition so as to form a discontinuous network of visible zones.

Figure 11:
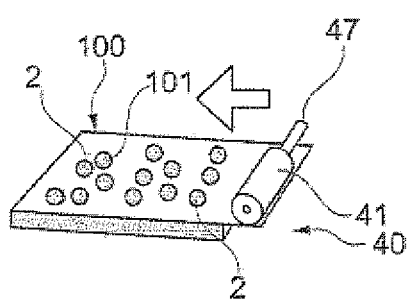
FIG. 11 illustrates, diagrammatically and partially, the production of an applicator that may be used in the context of the processes according to the invention bearing a discontinuous deposit of islets of corrective composition.

FIG. 11 shows an embodiment variant for obtaining an applicator 40 bearing on its application surface 41 a discontinuous deposit of islets 2 of corrective composition.

The applicator 40 has, for example, a smooth application surface 41 and is, as illustrated, in the form of a roller comprising a handle part 47.

A stencil 100 comprising holes 101 is, as illustrated, placed on a block of pulverulent corrective composition. The arrangement of the holes 101 is linked to the pattern of corrective composition to be obtained.

On contact with the stencil 100, the user moves the applicator 40 and a set of islets 2 of the corrective composition are thus deposited on the application surface 41.

The applicator 40 can then apply, onto a foundation deposit, the islets 2 of corrective composition so as to obtain a predefined pattern on the made-up surface.

Figure 11A:
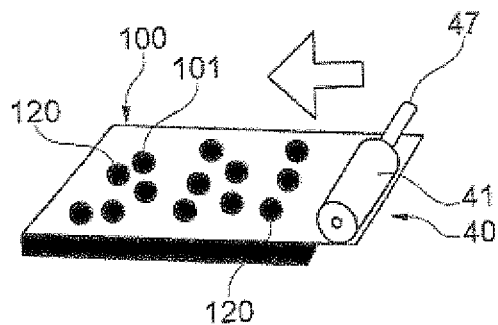
FIGS. 11A, 22A and 22B illustrate processes for manufacturing an example of a cosmetic device according to the invention.

FIG. 11A shows an embodiment variant for obtaining a device 40 bearing on its peripheral surface 41 a plurality of deposits of adhesive composition 120.

The device 40 has, for example, a smooth peripheral surface 41 and is, as illustrated, in the form of a roller comprising a handle part 47.

A stencil 100 comprising holes 101 is, as illustrated, placed on a block of pulverulent adhesive composition 120. The arrangement of the holes 101 is linked to the pattern to be obtained.

On contact with the stencil 100, the user moves the device 40 and a plurality of deposits of adhesive composition 120 are thus obtained on the peripheral surface 41.

The device 40 can then place a foundation deposit in contact with the adhesive composition 120 so as locally to take up the foundation and to obtain a predefined pattern on the made-up surface.

As a variant, as explained above, the block of adhesive composition 120 may be replaced with a block of product to be applied to keratin materials so as to obtain a device bearing, on its peripheral surface, a plurality of islets formed from a product that can transfer onto the skin.

Figure 12:
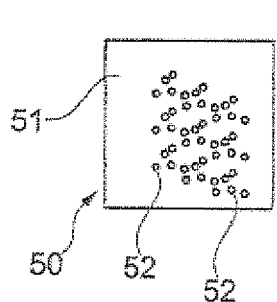

FIG. 12 shows a screen 50 with holes, consisting of a plate 51 comprising holes 52.

The arrangement of the holes 52 corresponds to a pattern to be reproduced, especially to an arrangement of freckles to be reproduced on the made-up surface.

Figure 13:
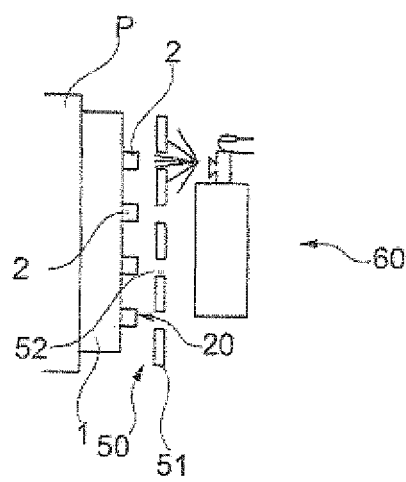

FIG. 13 illustrates the use of a process according to the invention in which a screen 50 with holes is placed against a deposit of foundation composition 1. A sprayer 60 is brought up to the screen 50 and sprays the corrective composition through the holes 52 so as to form a discontinuous deposit 20 of islets 2 of corrective composition.

As a variant, the corrective composition may be sprayed directly onto the skin so as to form a discontinuous deposit of islets of corrective composition or applied in a spatially non-uniform manner by the user.

A discontinuous deposit of islets of corrective composition may also be formed directly by using an inkjet printer. The printing devices described in FR 2 933 582 may generally be used.

FIGS. 14a and 14b illustrate another means that may be used for spraying the corrective composition 81 in the form of droplets onto the foundation deposit.

As illustrated in FIG. 14a, a brush 90 is used comprising a support 92 to which are connected flexible bristles 91. A toothed brush is used, for example. The bristles 91 bear the corrective composition 81. These bristles 91 are constrained as illustrated in FIG. 14a.

The bristles 91 are then released and return to their equilibrium position as illustrated in FIG. 14b; in so doing, the corrective composition 81 is sprayed in the form of droplets onto the surface to be treated.

FIG. 15 shows the application, in a first stage, of a continuous deposit 70 of corrective composition. As illustrated in FIG. 16, the corrective composition is configured so as to form a discontinuous deposit 20 of islets 2 after it has been applied to the foundation composition 1 via a surface tension phenomenon.

Figure 17:
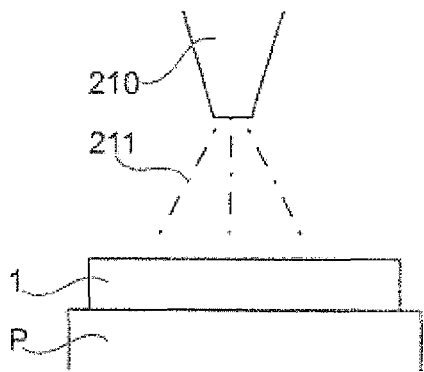
Figure 18:
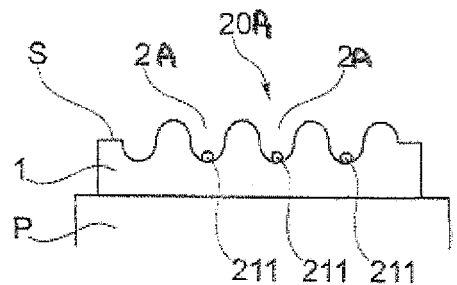

FIGS. 17 and 18 illustrate an embodiment variant of step b) according to the invention resulting in movement of the foundation due to the spraying of material.

In this case, a nozzle 210 for spraying a pulverulent composition comprising particles 211 is brought up to the foundation deposit 1. The particles 211 are sprayed onto the foundation composition 1 and, on impact, produce a variation of relief of the free surface S of the foundation 1 as illustrated in FIG. 18. This relief variation makes it possible to obtain the desired discontinuous network 20A of islets 2A.

As a variant, FIG. 18 shows a makeup result according to the invention in which particles 211 have been dispensed onto the foundation coat 1 by a device as illustrated in FIG. 7. In this case, the pins locally move the foundation and thus produce a modification of the shape of the free surface S of the foundation deposit 1 so as to form, as illustrated, a discontinuous network 20A of visible zones 2A, the pins also making it possible to move particles that are initially present in the reservoir 43.

Needless to say, as a variant, a medium in liquid form may be sprayed to obtain a relief variation due to the impact of drops onto the foundation.

As a variant, a solvent that is capable of dissolving the foundation composition may be sprayed in order especially to move the said foundation and to produce the desired pattern, and especially the desired discontinuous network of islets.

In a variant not shown, the foundation may be moved by spraying with compressed air.

Figure 19:
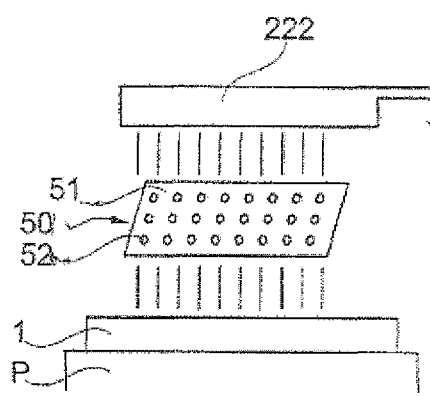
Figure 20:
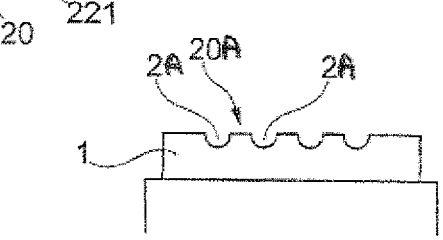

FIGS. 19 and 20 show an embodiment variant in which a plate 50 comprising holes 52 is placed against a foundation deposit 1.

A suction system 220 comprising a handle part 221 and a suction zone 222 is placed close to the foundation deposit 1 so that the plate 50 bearing holes is intercalated between the foundation 1 and the suction system 220.

Next, as shown in FIG. 19, the user starts the suction. Suction will take place mainly at the foundation zones aligned with the holes and the suction system. It will thus be possible locally to take up the foundation composition 1 by suction so as to obtain the desired discontinuous network 20A of islets 2A.

As a variant, a stencil may be applied to the deposit of foundation composition and a pad comprising an absorbent composition then applied over this stencil, the foundation being taken up by the absorbent composition through the holes of the stencil. The pattern then obtained on the foundation composition is linked to the arrangement of the holes in the stencil.

Figure 21:
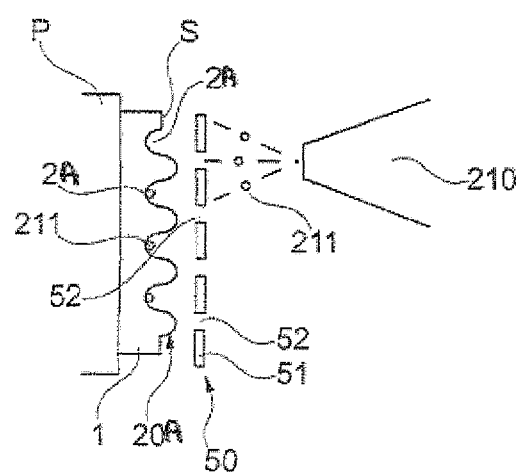

FIG. 21 shows a screen 50 with holes, consisting of a plate 51 comprising holes 52.

The arrangement of the holes 52 corresponds to a pattern to be reproduced, especially to an arrangement of freckles to be reproduced on the made-up surface.

FIG. 21 illustrates the use of a process according to the invention in which a screen 50 with holes is placed against a deposit of foundation composition 1. A nozzle 210 for spraying particles 211 is brought up to the screen 50 and sprays the said particles through the holes 52. On impact with the foundation 1, the particles 211 modify the form of the free surface S of the foundation deposit 1 so as to form, as illustrated, a discontinuous network 20A of islets 2A.

FIGS. 22A to 22D show different steps of a process according to the invention. A sprayer 122 is brought up to a support 123 and sprays thereon droplets 121 of an adhesive compound dissolved in a solvent.

Figure 22A:
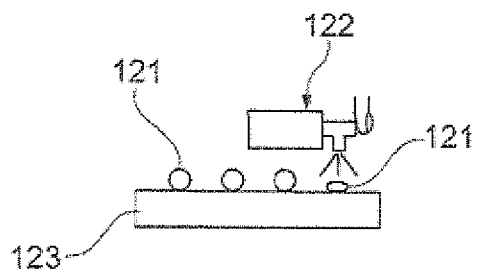
Figure 22B:
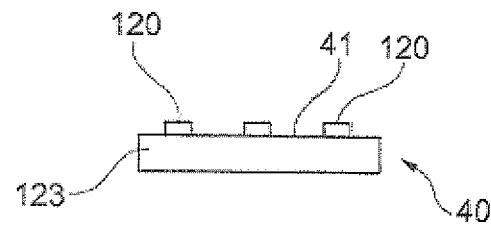

After the solvent has dried, the support shown in FIG. 22B is obtained, which comprises a plurality of deposits of an adhesive composition 120. This support constitutes an example of a device 40 according to the invention comprising a peripheral surface 41 on which are arranged islets, taking the form here of deposits of adhesive composition 120.

Figure 22C:
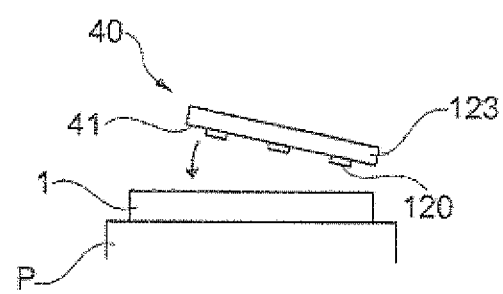
FIGS. 22C to 23C illustrate the various steps of processes for obtaining made-up surfaces according to the invention.
Figure 22D:
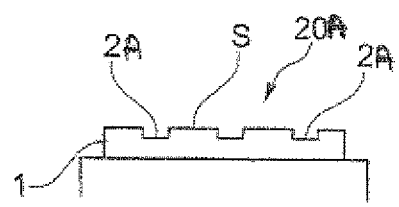

The support of FIG. 22B is placed in contact with a foundation deposit 1 as shown in FIG. 22C. A modification of the form of the free surface S of the foundation 1 is thus obtained due to the local uptake of the foundation by the deposits of adhesive composition.

A discontinuous network 20A of visible zones 2A whose arrangement is linked to the arrangement of the deposits of adhesive composition 120 on the support 123 and which makes it possible, for example, to reproduce the appearance of freckles may thus be obtained.

As a variant, droplets of a solid compound dissolved at high concentration in a solvent are sprayed onto a support. Next, after the solvent has dried, the solid compound present on the support is placed in contact with the foundation. The deposits of solid compound allow the movement of small portions of material, thus creating the desired pattern, and especially the desired discontinuous network of visible zones.

Figure 23A:
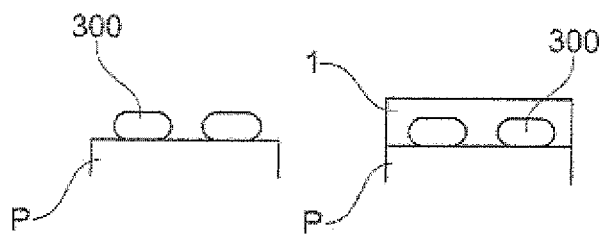
Figure 23B:
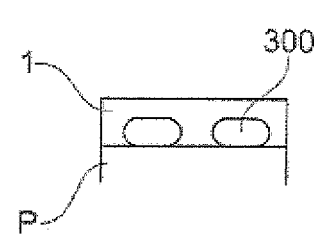
Figure 23C:
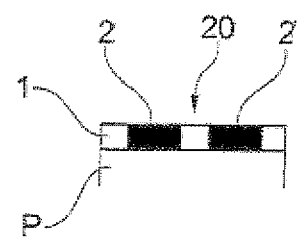

The purpose of FIGS. 23A to 23C is especially to show that the application of a product by the devices according to the invention may be performed before applying a foundation composition to the skin.

FIG. 23A shows the deposition onto a plurality of regions of the skin P of a chemical reagent 300. This deposition may be performed, for example, by means of the device 40 shown in FIG. 6 or 7.

The foundation composition 1 is then, as shown in FIG. 23B, applied to the skin P so as to be placed in contact with the chemical reagent 300.

FIG. 23C shows diagrammatically the discontinuous network 20 of visible zones 2 obtained after reaction of the chemical reagent 300 with a compound present in the foundation 1.

Figures 24, 25:
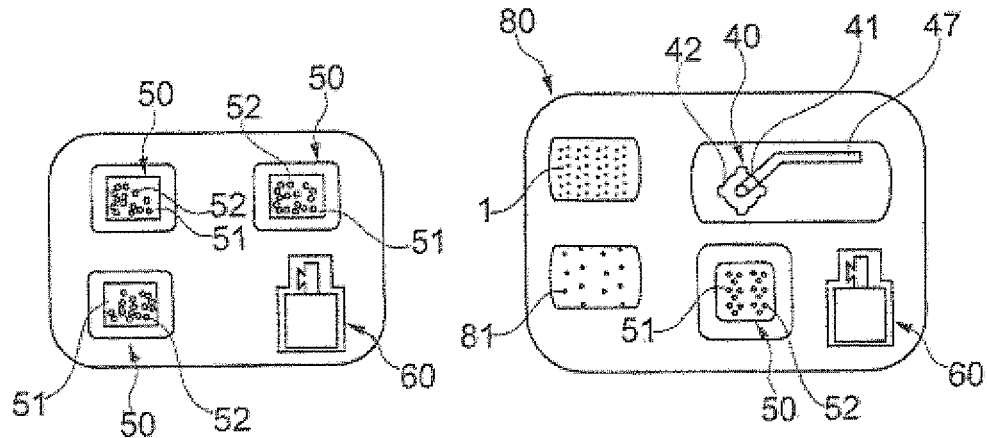
FIGS. 24 to 27 illustrate examples of a makeup kit according to the invention.

FIG. 24 shows a makeup kit according to the invention, comprising, in separate conditioning units:
- a pulverulent foundation composition 1,
- a particulate corrective composition 81,
- an applicator 40 comprising an application surface 41 bearing pins 42 for applying the corrective composition to a foundation deposit,
- a screen 50 consisting of a plate 51 with holes 52, the arrangement of the holes reproducing, for example, a freckle pattern to be obtained, and
- a sprayer 60 for applying a corrective composition in the form of droplets onto a foundation deposit 1.

As a variant, a makeup kit according to the invention comprises, in separate conditioning units:
- a pulverulent foundation composition 1,
- a device 40 comprising a surface 41 bearing pins 42 for moving and/or taking up foundation present on the skin,
- a screen 50 consisting of a plate 51 with holes 52, the arrangement of the holes reproducing, for example, a freckle pattern to be obtained, and
- a spraying system 60 for applying material, especially droplets, onto a foundation so as locally to move the latter.

FIG. 25 shows a makeup kit according to the invention comprising a corrective composition sprayer 60 and a set of screens 50 bearing holes, in which the arrangement of the holes 52 is linked to a corrective composition pattern to be obtained.

The various screens 50 present in this assembly differ in the arrangement of the holes 52.

Thus, the user can choose a corrective composition pattern to be obtained, for example a predefined freckle pattern, by choosing a screen 50 rather than another one.

The invention thus makes it possible to personalize the makeup.

Figure 26:
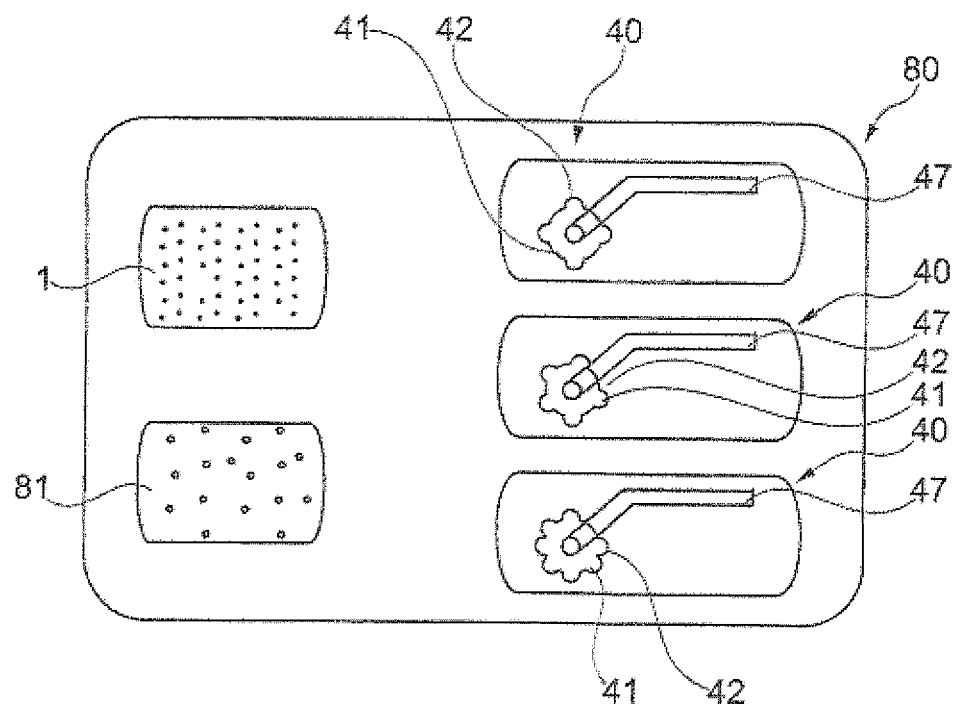
Figure 27:
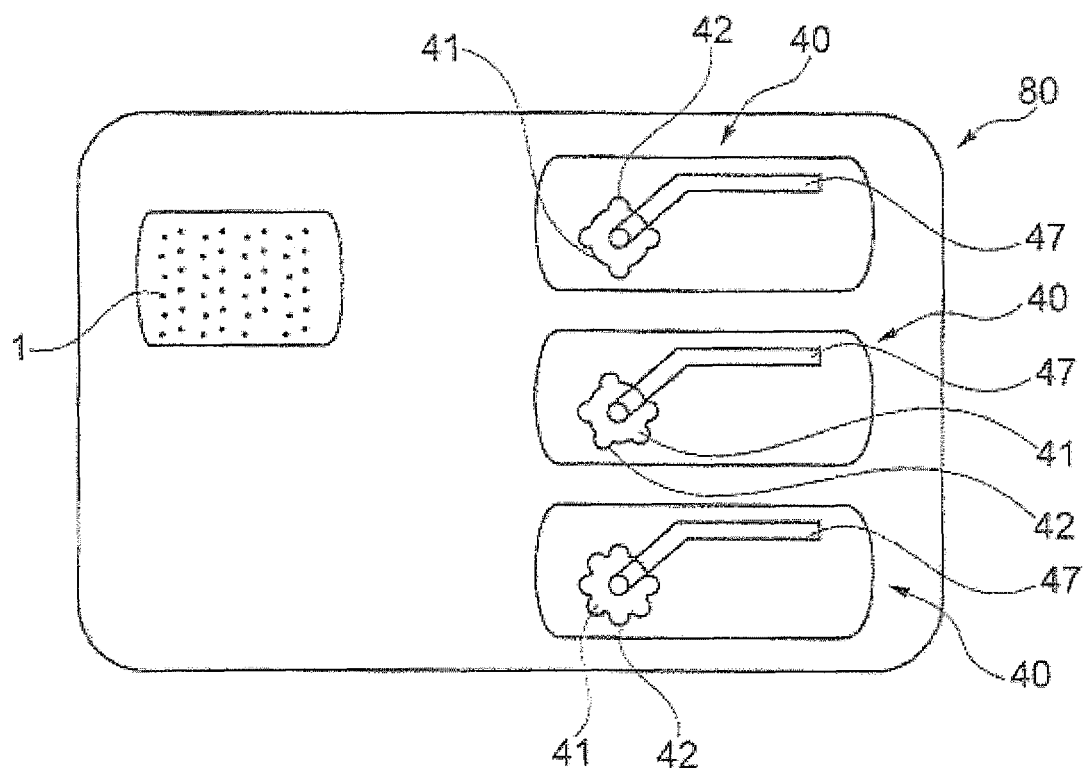

FIGS. 26 and 27 show an assembly 80 according to the invention comprising a plurality of devices 40 and also a foundation product 1 to be applied with the aid of these devices 40. The devices 40 differ in the arrangement of the pins 42 on the peripheral surface 41. Thus, each device allows the production of a different pattern on a surface of made-up skin.

Before performing the process according to the invention, the user can choose a device from within this assembly 80, which allows him to choose to produce a predefined pattern.

EXAMPLES

Example 1

A first, very covering foundation (Dermablend Professional, light colour) is first applied. At this stage, the irregularities are hidden but the appearance cannot be considered as being natural.

A roller is then used as described in FIG. 6. Small spots of brown foundation ("Infaillible" dark shade) about 1 mm wide are placed on the pins.

The roller is then rolled over the skin on the cheeks and the forehead. Transfer of the small spots is obtained, producing a natural effect.

At the end of the treatment, the colour differences are attenuated slightly by stroking lightly with a pad of cotton wool or by using a brush.

Example 2

An application session directed towards evaluating the effects of a base comprising small coloured fibres superposed on a very covering foundation was performed.

Although a covering foundation makes it possible to obtain very efficient masking of dyschromia, this foundation has the effect of making the complexion look dull and unnatural.

Tinted creams comprising small coloured fibres were applied onto a coat of covering foundation. The compositions of these tinted creams are given below.

| | Tinted cream 1 | Tinted cream 2 |
|---|---|---|
| 0.1 mm to 0.75 mm red cellulose fibres (Rayon) from the company Claremont Flock | 6 | |
| 0.1 mm to 0.75 mm brown cellulose fibres (Rayon) from the company Claremont Flock | | 6 |
| Polyacrylamidomethylpropanesulfonic acid partially neutralized with aqueous ammonia and highly crosslinked (Hostacerin AMPS from Clariant) | 1 | 1 |
| PDMS 10 cSt (Xiameter PMX-200 Silicone Fluid 10 CS from Dow Corning) | 11 | 11 |
| PEG-12 dimethicone (Silsoft 880 from Momentive Performance Materials) | 0.7 | 0.7 |
| Alcohol | 8 | 8 |
| Water | qs 100 | qs 100 |

|  | Tinted cream 1 | Tinted cream 2 |
| --- | --- | --- |
| Glycerol | 7 | 7 |
| Propylene glycol | 2 | 2 |
| Preserving agent | 0.4 | 0.4 |

When applied onto different foundations (Vichy Normaderm Teint, Dermablend Nude, Dermablend Professional), the tinted creams optimize the homogeneity of the film, especially as regards the colour result.

They produce better melting of the tinted film of these various makeup products into the skin, affording a more natural, less caked-on makeup result.

Example 3

Example with a Corrective Composition in Fluid Form During its Application and Comprising a Volatile Solvent A foundation is applied to the skin and the coat is left to stand for a few minutes. A composition formed from dimethyl ether (60%), water (20%), ethanol (18%) and a brown dye (caramel) (2%) is then sprayed on.

Evaporation leaves small beige islets showing through on the foundation coat.

Example 4

Example with a Discontinuous Deposit of Islets Obtained Via a Surface Tension Phenomenon A foundation into which perfluoropolyether particles (Fomblin) have been introduced is applied. The entirety covers the skin uniformly. Next, a fluid aqueous composition containing a brown dye (caramel) (2%) is sprayed on. After a few seconds, the aqueous composition evaporates, leaving small beige islets on the coating formed by the foundation.

Example 5

Example with a Discontinuous Deposit of Islets Obtained by Applying an Electric and/or Magnetic Field and/or a Positive Pressure after Application of the Corrective Composition Iron filings (grains 0.1 mm on average) are incorporated into a foundation at a rate of 1 g per 100 g of composition.

Next, after applying to the face, the same foundation is applied as an overcoat onto the surface of the cheek. The makeup is left to stand for about 5 minutes. Next, a rare-earth metal magnet 1.4 cm in diameter and generating a magnetic field with strength of 1.1 Tesla is placed 4 cm from the skin. After a few seconds, the magnet is removed. The magnetic field moves the particles slightly, causing them to appear especially at the centre of the cheek.

Example 6

A covering, water-based first foundation is applied. At this stage, the irregularities are hidden but the appearance is not natural.

Next, a roller is used as described in FIG. 6 (3 cm in diameter). The pins are capable of depositing magnesia particles. Each particle is about 1 mm in size. The roller is rolled over a bed of magnesia. The roller is then rolled over the skin on the cheeks and the forehead. A transfer of small spots is obtained, producing a natural effect.

In one particular option, the system contains a magnesia powder dispenser as shown in FIG. 7.

Example 7

The makeup obtained in Example 6 is stroked lightly with a brush in order to take up or detach material in the areas where the magnesia has been deposited.

Example 8

A makeup is produced according to Example 6. The nozzle of a Dyson model DC30 cordless vacuum cleaner is then brought to within 2 cm of the makeup deposit produced. This vacuum cleaner develops a power of about 300 W.

Local removal of material at the areas where the magnesia has been deposited is then produced, by suction.

Example 9

A powder foundation ("Accord parfait" from L'Oréal Paris) is applied. Four coats are successively applied in order to create a thick coat.

At this stage, the irregularities are hidden but the appearance is not very natural.

Next, the roller described in FIG. 6 (3 cm in diameter) is used. The pins are made of an absorbent material based on Nylon® flocking comprising a mixture of fibres 200 µm and 10 µm in diameter bonded together on a support. Each pin is 5 mm long and has a tip diameter of 1 mm.

The roller is rolled over the skin on the cheeks and the forehead. The foundation is then removed locally so as to produce a natural effect.

Before reusing the roller for treating another area of the face, it is cleaned.

Example 10

A tool formed from a platform perforated with 16 holes is produced. 16 stems pass through the holes, and are driven by a motor and a set of gears.

Thus, when the front face is observed, 16 stems are seen, protruding one millimetre above the platform.

One flocked slug 1 mm in size is bonded to each stem.

A thick coat of foundation is applied.

The platform is brought to the skin for one second and the makeup is very lightly stroked. The creation of small grains that enhance the makeup is observed.

Example 11

An entirely lipophilic foundation is applied. It is a mixture of PDMS silicone (44%), volatile silicone (D5) (26%) and white and brown pigments.

A device formed from a chamber, connected on one side to a compressed air inlet and on the other side to a concave membrane (in the shape of the cheek) pierced with 61 holes each 0.3 mm in diameter, is brought up. The membrane is solidly attached to the chamber and has an area of 16 cm².

After applying the foundation, the user brings the device (membrane side) to within about ½ cm of the skin and applies a jet of compressed air (2 bar) for 1 sec.

He then removes the device and applies a stream at low pressure (0.5 bar) at a greater distance (3 cm) to flush the skin gently.

After final drying, it is seen that the coat has small grains.

Example 12

Granular citric acid powder is placed in the same device as above. The grains each have a size of about 0.3 mm.

These grains are sprayed onto skin covered with an emulsion-based foundation.

Example 13

Acetone is placed in the same device as above.

The acetone is sprayed onto skin covered with a foundation based on acrylate polymer (Resin 28-2930 from the company Akzo Nobel) and on pigment.

Example 14

A foundation based on emulsion and ferrite grains (8%) is produced.

A rare-earth metal magnet of 1.1 Tesla is broken into pieces with a hammer.

The small pieces of magnet (about 1 mm each) are bonded using Araldite® glue onto a 16 cm² solid membrane.

After applying the foundation and before total drying, the membrane is brought up to the skin. After 1 second, the membrane is removed. Grains are observed in the coating.

Example 15

A covering, water-based first foundation is applied. At this stage, the irregularities are hidden but the appearance is not natural.

Next, a roller as illustrated in FIG. 7 (3 cm in diameter) is used. The reservoir placed in contact with the roller pins is a small metal chest (aluminium) 5 cm wide, 5 cm long and 1 cm deep. It contains a lipstick formulation. The small metal chest also comprises a small piston that can be manually actuated to advance the lipstick formulation towards the outlet in order to ensure contact with the pins during its use. The pins are capable of creating a negative pressure in the foundation and of depositing spots of colour. Each particle is about 1 mm in size. The roller is rolled over the skin on the cheeks and the forehead. A transfer of small spots is obtained, producing a natural effect.

Example 16

A very covering first foundation is applied.

At this stage, the irregularities are hidden but the appearance is not natural.

Next, a roller as illustrated in FIG. 6 (3 cm in diameter) is used. The pins are made of an absorbent material, using cardboard finely cut into small cylindrical sticks. Each pin is 3 mm tall and has a diameter of 1 mm at its tip and at its base. On contact, the pins absorb some of the foundation.

The roller is rolled over the skin on the cheeks and the forehead. The foundation is then removed locally so as to produce a natural effect.

Before reusing the roller for treating another area of the face, it is cleaned.

Example 17

A very covering first foundation is applied. It contains polyvinylamine (Lupamine® from BASF) in a proportion of 4% of active material.

At this stage, the irregularities are hidden but the appearance is not natural.

Next, a roller as illustrated in FIG. 6 is used. The tips are made of an absorbent material. DHA is deposited in the tips. The roller is rolled over the skin on the cheeks and the forehead. Small spots are obtained, producing a natural effect.

Characteristics described within illustrated variants may be combined with variants not illustrated.

The expression "comprising a" should be understood as meaning "comprising at least one".

The expressions "between" or "ranging from . . . to . . . " should be understood as including the limits.

The invention claimed is:

1. A method for making up skin comprising forming on a deposit of a foundation composition applied to the skin a discontinuous deposit of islets of corrective composition,
said corrective composition comprising a red dye and having optical properties that locally modify appearance of makeup so as to create a pattern reproducing appearance of skin relief and/or colour heterogeneities,
the islets comprising at the same time islets having a largest dimension between 0.8 and 2 mm, islets having a largest dimension greater than 2 mm and less than or equal to 3 mm and islets having a largest dimension greater than 3 mm and less than or equal to 5 mm,
a number of islets having a largest dimension between 0.8 and 2 mm being greater than a number of islets having a largest dimension greater than 2 mm and less than or equal to 3 mm and greater than a number of islets having a largest dimension greater than 3 mm and less than or equal to 5 mm.

2. The method according to claim 1, the islets comprising adjacent islets, the spacing between which is greater than or equal to 2 mm.

3. Kit comprising:
a) a foundation composition, and
b) a corrective composition, the corrective composition being coloured and further comprising a red dye, and
c) an applicator for the application of said corrective composition onto a surface to be made up,
the applicator comprising an application surface comprising a network of zones having corrective composition-releasing properties, which is configured to form, during application onto the surface to be made up, a pattern that reproduces the appearance of skin colour and/or relief heterogeneities, said pattern comprising a discontinuous deposit of islets and/or the applicator making it possible to spray the corrective composition so as to form a discontinuous deposit of islets, and/or an arrangement of holes in a screen bearing the holes and forming a stencil against the surface to be made up being linked to a pattern that reproduces the appearance of the skin colour and/or relief heterogeneities to be obtained, said pattern comprising a discontinuous deposit of islets,
the islets comprising at the same time islets having a largest dimension between 0.8 and 2 mm, islets having a largest dimension greater than 2 mm and less than or equal to 3 mm and islets having a largest dimension greater than 3 mm and less than or equal to 5 mm,
a number of islets having a largest dimension between 0.8 and 2 mm being greater than a number of islets having a largest dimension greater than 2 mm and less than or equal to 3 mm and greater than a number of islets having a largest dimension greater than 3 mm and less than or equal to 5 mm.

4. Kit according to claim 3, the corrective composition comprising visible substances that give it an inhomogeneous appearance, said visible substances being coloured fibres.

5. Kit according to claim 3, comprising
a device for locally removing and/or moving foundation deposited on the skin,
the device comprising a surface comprising a network of zones for removing and/or moving foundation so as to form a pattern that reproduces the appearance of skin colour and/or relief heterogeneities.

6. Process for making up the skin, comprising:
a) applying a foundation composition to the skin, and
b) locally removing the foundation applied in step a) so as to create a pattern reproducing the appearance of skin relief and/or colour heterogeneities, said pattern comprising a discontinuous deposit of islets,
the islets comprising at the same time islets having a largest dimension between 0.8 and 2 mm, islets having a largest dimension greater than 2 mm and less than or equal to 3 mm and islets having a largest dimension greater than 3 mm and less than or equal to 5 mm, and
a number of islets having a largest dimension between 0.8 and 2 mm being greater than a number of islets having a largest dimension greater than 2 mm and less than or equal to 3 mm and greater than a number of islets having a largest dimension greater than 3 mm and less than or equal to 5 mm.

7. The process according to claim 6, said islets being defined by a liquid.

8. The process according to claim 6, the islets comprising adjacent islets, the spacing between which is greater than or equal to 2 mm.

9. Cosmetic device having a peripheral surface comprising islets arranged non-uniformly in a surrounding surface, said islets each having a largest dimension of at least 0.8 mm and having a shape and/or properties for taking up and/or releasing a product present on the skin or to be applied thereto that are different from the shape and/or properties of the surrounding surface, so as to lead to the creation on the skin of a pattern whose appearance is linked to the arrangement of the islets on the surface,
the islets comprising at the same time islets having a largest dimension between 0.8 and 2 mm, islets having a largest dimension greater than 2 mm and less than or equal to 3 mm and islets having a largest dimension greater than 3 mm and less than or equal to 5 mm, and
a number of islets having a largest dimension between 0.8 and 2 mm being greater than a number of islets having a largest dimension greater than 2 mm and less than or equal to 3 mm and greater than a number of islets having a largest dimension greater than 3 mm and less than or equal to 5 mm.

10. Device according to claim 9, the islets being in relief and protruding relative to the surrounding surface.

11. Device according to claim 9, the islets having physicochemical properties different from those of the surrounding surface.

12. Device according to claim 9, said islets having properties for capturing and/or releasing a product present on the skin or to be applied thereto that are different from the properties of the surrounding surface.

13. Device according of claim 9, the islets being defined with the aid of pins that can be moved relative to the surrounding surface.

14. Device according to claim 13 said movable pins being defined by electrically driven actuators.

15. Device according to claim 9, the islets being defined by grains of a product that can be transferred to the skin.

16. Device according to claim 9, the islets being defined by a liquid.

17. Device according to claim 9, comprising islets having a largest dimension greater than or equal to 2 mm.

18. Device according to claim 9, comprising islets of circular contour.

19. Device according to claim 9, comprising islets that are touching and islets that are separate.

20. Device according to claim 9, comprising islets of non-circular contour.

21. Device according to claim 9 comprising islets of circular contour in a number greater than that of a number of islets of non-circular contour.

22. Device according to claim 9, comprising adjacent islets, the spacing between which is greater than or equal to 2 mm.

23. Assembly comprising a device as defined in claim 9 and a makeup product intended to be applied to the skin by means of said device.

24. Kit comprising a device as defined in claim 9 and a master surface for creating islets on the surface, having some zones loaded with product and/or others without product.

25. Process for making up the skin, comprising a step of moving and/or taking up a product present on the skin and/or a step of applying a product to the skin by means of a device according to claim 9, for creating visible zones whose distribution corresponds to that of the islets on the peripheral surface.

26. Process according to claim 25, the visible zones being created by application of a product to the skin.

27. Process according to claim 26, the product comprising a red dye.

28. Process according to claim 25, the visible zones being created by removal of product on the skin.

29. Process according to claim 25, comprising a prior application to the skin of a foundation, the visible zones being created on a deposit of foundation.

30. Process according to claim 25, a treatment using the device being performed without sliding of the peripheral surface over the optionally made-up skin.

31. Process according to claim 30, the treatment being performed by rolling the peripheral surface over the optionally made-up skin.

32. Process according to claim 25, a discontinuous network of visible zones being created.

33. The cosmetic device according to claim 9, said islets being defined by a liquid.

34. The cosmetic device according to claim 9, the islets comprising adjacent islets, the spacing between which is greater than or equal to 2 mm.

35. Process for making up skin comprising forming, on a deposit of a foundation composition applied to the skin, a deposit of a liquid corrective composition comprising visible substances that give it an inhomogeneous appearance,
said corrective composition comprising a red dye and having optical properties that locally modify appearance of makeup so as to create a pattern reproducing appearance of skin relief and/or colour heterogeneities, said pattern comprising a discontinuous deposit of islets,
the islets comprising at the same time islets having a largest dimension between 0.8 and 2 mm, islets having a largest dimension greater than 2 mm and less than or equal to 3 mm and islets having a largest dimension greater than 3 mm and less than or equal to 5 mm, and a number of islets having a largest dimension between 0.8 and 2 mm being greater than a number of islets having a largest dimension greater than 2 mm and less than or equal to 3 mm and greater than a number of islets having a largest dimension greater than 3 mm and less than or equal to 5 mm.

36. The method according to claim 1, said islets being defined by a liquid.

* * * * *